(12) United States Patent
Hammond et al.

(10) Patent No.: US 8,198,296 B2
(45) Date of Patent: Jun. 12, 2012

(54) SUB-TYPE SELECTIVE AZABICYCLOALKANE DERIVATIVES

(75) Inventors: Philip S. Hammond, Pinnacle, NC (US); Anatoly Mazurov, Greensboro, NC (US); Yun-De Xiao, Clemmons, NC (US); Srinivasa V. Murthy, Winston-Salem, NC (US); Srinivisa Rao Akireddy, Winston-Salem, NC (US)

(73) Assignee: Targacept, Inc., Winston-Salem, NC (US)

( * ) Notice: Subject to any disclaimer, the term of this patent is extended or adjusted under 35 U.S.C. 154(b) by 155 days.

(21) Appl. No.: 12/593,779

(22) PCT Filed: Mar. 27, 2008

(86) PCT No.: PCT/US2008/058384
§ 371 (c)(1),
(2), (4) Date: Feb. 26, 2010

(87) PCT Pub. No.: WO2008/121686
PCT Pub. Date: Oct. 9, 2008

(65) Prior Publication Data
US 2010/0173968 A1 Jul. 8, 2010

Related U.S. Application Data

(60) Provisional application No. 60/909,030, filed on Mar. 30, 2007.

(51) Int. Cl.
*A61K 31/439* (2006.01)
*C07D 221/22* (2006.01)
*C07D 221/02* (2006.01)

(52) U.S. Cl. .................................. 514/299; 546/112

(58) Field of Classification Search .................. 546/112; 514/299
See application file for complete search history.

(56) References Cited

U.S. PATENT DOCUMENTS

| | | | |
|---|---|---|---|
| 4,922,901 A | 5/1990 | Brooks et al. |
| 5,583,140 A | 12/1996 | Bencherif et al. |
| 5,597,919 A | 1/1997 | Dull et al. |
| 5,604,231 A | 2/1997 | Smith et al. |
| 5,616,716 A | 4/1997 | Dull et al. |
| 5,663,356 A | 9/1997 | Ruecroft et al. |
| 5,852,041 A | 12/1998 | Cosford et al. |
| 5,853,696 A | 12/1998 | Elmaleh et al. |
| 5,952,339 A | 9/1999 | Bencherif et al. |
| 5,969,144 A | 10/1999 | London et al. |

FOREIGN PATENT DOCUMENTS

| | | |
|---|---|---|
| WO | WO 94/08992 | 4/1994 |
| WO | WO 96/31475 | 10/1996 |
| WO | WO 96/40682 | 12/1996 |
| WO | WO-98/54182 | 12/1998 |
| WO | WO-01/44243 | 6/2001 |
| WO | WO 2004/016604 | 2/2004 |
| WO | WO-06/96358 | 9/2006 |

OTHER PUBLICATIONS

Schafer et al. Drug Discovery Today 2008, 13 (21/22), 913-916.*
Horig et al. Journal of Translational Medicine 2004, 2(44).*
Medicines in Development for Mental Illnesses 2010.*
International Search Report, Jul. 16, 2008, PCT.
Becker, D.P. and D.L. Flynn, "Synthesis of N-BOC-3-Azabicyclo[3.3.0]octan-7-one via Reductive Pauson-Khand Cyclization and Subsequent Conversion to a Novel Diazatricyclic Ring System," *Tetrahedron Letters*,49(23): 5047-5054 (1993).
Becker, D.P., et al., "Synthetic Strategies for the Construction of Enantiomeric Azanoradamantanes," *Tetrahedron Letters*, 53(1): 1-20 (1997).
Flynn, D.L., et al., "Use of Methyl 2-Iodo-2-(Phenylsulfonyl)-4-Pentenoate in Atom-Transfer Radical Cyclizations," *Tetrahedron Letters*, 33(48): 7281-7282 (1992).
Flynn, D.L. and D.L. Zabrowski, "Halogen Atom Transfer Annulations Involving Iodomalonates and Allylamine Derivatives," *J. Org. Chem.*, 55: 3673-3674 (1990).
Kiso, Y. and H. Yajima, "Amide Formation, Deprotection, and Disulfide Formation in Peptide Synthesis," *Peptides, Synthesis Structures and Applications*, 39-91 (1995).
Minakata, S., et al., "Introduction of an N1 Unit to Monoenes or 1,6-Dienes Using Choramine-T-Silver Nitrate: A New Route to Aziridines or Bicyclic Pyrrolidines," *Heterocycles*, 60(2): 289-298 (2003).
Peterson, E.M., et al., "a-Spirocyclopentyl-and a-Spirocyclopropyl-y-butyrolactones: Conformationally Constrained Derivatives of Anticonvulsant and Convulsant a,a-Disubstituted-y-Butyrolactones," *J. Med. Chem.*, 37: 275-286 (1994).
Romano, C. and A. Goldstein, "Stereospecific Nicotine Receptors on Rat Brain Membranes," *Science*, 210: 647-649 (1990).

(Continued)

*Primary Examiner* — Jason M Nolan
(74) *Attorney, Agent, or Firm* — Amy H. Fix

(57) ABSTRACT

Compounds, pharmaceutical compositions including the compounds, and methods of preparation and use thereof are disclosed. The compounds are amide, ketone, and ester compounds prepared from certain azabicycloalkane carboxylic acids. The resulting compounds exhibit selectivity for, and bind with high affinity to, neuronal nicotinic receptors of the α4β2 subtype in the central nervous system (CNS). The compounds and compositions can be used to treat and/or prevent a wide variety of conditions or disorders, such as those disorders characterized by dysfunction of nicotinic cholinergic neurotransmission, including disorders involving neuromodulation of neurotransmitter release, such as dopamine release. CNS disorders, which are characterized by an alteration in normal neurotransmitter release, are another example of disorders that can be treated and/or prevented. The compounds can: (i) alter the number of nicotinic cholinergic receptors of the brain of the patient, (ii) exhibit neuroprotective effects, and (iii) when employed in effective amounts, not result in appreciable adverse side effects (e.g. side effects such as significant increases in blood pressure and heart rate, significant negative effects upon the gastrointestinal tract, and significant effects upon skeletal muscle).

5 Claims, 2 Drawing Sheets

OTHER PUBLICATIONS

Speckamp, W.N., et.al., "Synthesis of Substituted 3-Aza-Bicyclo[3.3.1]Nonanes," *Tetrahedron Letters*, 27: 3143-3156 (1971).

Stetter, H. and W. Reinartz, "Contribution to the Chemistry of 1-Azadamantane," *Chemische Berichte*, 105(9): 2773-2779 (1972).

Marks, M.J., et al., "Nicotinic Binding Sites in Rat and Mouse Brain: Comparison of Acetylcholine, Nicotine, and a-Bungarotoxin," *Molecular Pharm.*, 30: 427-436 (1986).

Newhouse, P.A., et al., "Effects of Nicotinic Stimulation on Cognitive Performance," *Current Opin. in Pharm.*, 4:36-46 (2004).

Arneric, S., et al., "Preclinical Pharmacology of ABT-418: A Prototypical Cholinergic Channel Activator for the Potential Treatment of Alzheimer's Disease," *CNS Drug Rev.*, 1(1): 1-26 (1995).

Arneric, S., et al., "Cholinergic channel modulators as a novel therapeutic strategy for Alzheimer's disease," *Exp. Opin. Invest. Drugs*, 5(1): 79-100 (1996).

Bannon, A.W., et al., "Broad-Spectrum, Non-Opioid Analgesic Activity by Selective Modulation of Neuronal Nicotinic Acetylcholine Receptors," *Science*, 279: 77-80 (1998).

Bencherif, M., et al., "RJR-2403: A Nicotinic Agonist with CNS Selectivity I: In Vitro Characterization," *J. Pharmacol. Exper. Therapeutics*, 279(3): 1413-1421 (1996).

Bencherif, M., and R.J. Lukas, "Ligand Binding and Functional Characterization of Muscarinic Acetylcholine Receptors on the TE671/RD Human Cell Line," *J. Pharmacol. Exp. Ther.* 257(3): 946-953 (1991).

Bencherif M. and R.J. Lukas, "Differential Regulation of Nicotinic Acetylcholine Receptor Expression by Human TE671/RD Cells Following Second Messenger Modulation and Sodium Butyrate Treatments," *Mol Cell Neurosci.*, 2(1): 52-65 (1991).

Bencherif, M., and J. D. Schmitt, "Targeting Neuronal Nicotinic Receptors: a Path to New Therapies," *Current Drug Targets 1*(4): 349-357 (2002).

Breining, S.R. et al., "Neuronal Nicotinic Acetylcholine Receptor Modulators: Recent Advances and Therapeutic Potential," *Annual Reports in Medicinal Chemistry*, vol. 40: 3-16 (2005).

Cheng, Yung-Chi, and W.H. Prusoff, "Relationship Between the Inhibition Constant ($K_1$) and the Concentration of Inhibitor which Causes 50 Per Cent inhibition ($I_{50}$) of an Enzymatic Reaction," *Biochem. Pharmacol.* 22(23): 3099-3108 (1973).

Chiari, A., et al., "Sex Differences in Cholinergic Analgesia I: A Supplemental Nicotinic Mechanism in Normal Females," *Anesthesiology*, 91(5): 1447-1454 (1999).

Coe, J.W. et al., "3,5-Bicyclic aryl piperidines: A novel class of α4β2 neuronal nicotinic receptor partial agonists for smoking cessation," *Bioorganic & Medicinal Chemistry Letters*, 15(22): 4889-4897 (2005).

Damaj, M.I., et al., "Antinociceptive and Pharmacological Effects of Metanicotine, a Selective Nicotinic Agonist," *J. Pharmacol. Exp. Ther.*, 291(1): 390-398 (1999).

Damaj, M.I., et al. << Enantioselective Effects of Hydroxy Metabolites of Bupropion on Behavior and on Function of Monoamine Transporters and Nicotinic Receptors,>> *Molecular Pharmacology*, 66(3) 675-682 (2004).

Dani, J.A. et al. << Potential applications of nicotinic ligands in the laboratory and clinic, >> *Bioorganic & Medicinal Chemistry Letters* 14 : 1837-1839 (2003).

Davies, Andrew R.L., et al., "Characterisation of the binding of [$^3$H]methyllycaconitine: a new radioligand for labeling α7-type neuronal nicotinic acetylcholine receptors," *Neuropharmacol.* 38: 679-690 (1999).

Decker, M.W., "Nicotinic Acetylcholine Receptor Agonists: A Potential New Class of Analgesics," *Current Topics in Medicinal Chemistry*, 4: 369-384 (2004).

Dwoskin, L.P. and Crooks, P.A., "A novel mechanism of action and potential use for lobeline as a treatment for psychostimulant abuse," *Biochemical Pharmacology*, 63: 89-98 (2002).

Graham, A.J., et al. "Human Brain Nicotinic Receptors, their Distribution and Participation in Neuropsychiatric Disorders," *Current Drug Targets-CNS & Neurological Disorders*, 1: 387-397 (2002).

Greene, T.W. and P.G. M. Wuts, "Protective Groups in Organic Synthesis," $3^{rd}$ ed. (1999).

Hogg, R.C. and Bertrand, D., "Nicotinic Acetylcholine Receptors as Drugs," *Current Drug Targets—CNS & Neurological Disorders*, 3: 123-130 (2004).

Holladay, M.W., et al., "Neuronal Nicotinic Acetylcholine Receptors as Targets for Drug Discovery," *J. Med. Chem.*, 40(26): 4169-4194 (1997).

Hoyer, D. and H.W.G.M. Boddeke, "Partial agonists, full agonists, antagonists: dilemmas of definition," *TiPS Reviews*, 14: 270-275 (1993).

Jain, K.K., "Modulators of nicotinic acetylcholine receptors as analgesics," *Current Opinion in Investigational Drugs*, 5(1): 76-81 (2004).

Jonnala, R.R. and Buccafusco, J.J., "Relationship Between the Increased Cell Surface α7 Nicotinic Receptor Expression and Neuroprotection Induced by Several Nicotinic Receptor Agonists," *Journal of Neuroscience Research*, 66: 565-572 (2001).

Lavand'homme, P.M., and J.C. Eisenach, "Sex Differences in Cholinergic Analgesia II: Differing Mechanisms in Two Models of Allodynia," *Anesthesiology*, 91(5): 1455-1461 (1999).

Levin, E.D., and A.H. Rezvani, "Nicotinic Treatment for Cognitive Dysfunction," *Current Drug Targets: CNS and Neurological Disorders*, 1(4): 423-431 (2002).

Li, M.D., et al., "Nicotine, Body Weight and Potential Implications in the Treatment of Obesity," *Current Topics in Medicinal Chemistry*, (3): 899-919 (2003).

Lippiello, P.M., et al., "RJR-2403: A Nicotinic Agonist with CNS Selectivity II. In Vivo Characterization," *J. P. E. T.*, 279(3): 1422-1429 (1996).

Lowry, et al., "Protein Measurement with the Folin Phenol Reagent," *J. Biol. Chem.* 193: 265-275 (1951).

Lukas, R.J., and M.J. Cullen, "An Isotopic Rubidium Ion Efflux Assay for the Functional Characterization of Nicotinic Acetylcholine Receptors on Clonal Cell Lines," *Anal. Biochem.* 175(1): 212-218 (1988).

Lukas, R.J., "Pharmacological Distinctions between Functional Nicotinic Acetylcholine Receptors on the PC12 Rat Pheochromocytoma and the TE671 Human Medulloblastoma," *J. Pharmacol. Exp. Ther.* 251(1): 175-182 (1989).

Lukas, R.J., et al., "Characterization of Nicotinic Acetylcholine Receptors Expressed by Cells of the SH-SY5Y Human Neuroblastoma Clonal Line," *Molec Cellular Neurosci* 4(1): 1-12 (1993).

Luther, et al., "A Muscle Acetylcholine Receptor is Expressed in the Human Cerebellar Medulloblastoma Cell Line TE671," *J. Neurosci.* 9(3): 1082-1096 (1989).

Marrero, M.B. et al., "The Neuroprotective Effect of 2-(3-Pyridyl)-1-azabicyclo[3.2.2]nonane (TC-1698), a Novel α7 Ligand, Is Prevented through Angiotensin II Activation of a Tyrosine Phosphatase," *The Journal of Pharmacology and Experimental Therapeutics*, vol. 309 (1) 16-27 (2003).

McEvoy, J.P. and Allen, T.B., "The Importance of Nicotinic Acetylcholine Receptors in Schizophrenia, Bipolar Disorder and Tourette's Syndrome," *Current Drug Targets—CNS & Neurological Disorders*, 1: 433-442 (2002).

Miao, F.J..P. et al. "Central Terminals of Nociceptors are Targets for Nicotine Suppression of Inflammation," Neuroscience, 123: 777-784 (2004).

O'Neill, M.J., et al., "The Role of Neuronal Nicotinic Acetylcholine Receptors in Acute and Chronic Neurodegeneration," *Current Drug Targets: CNS and Neurological Disorders*, 1(4): 399-411 (2002).

Oswald, R.E., et al., "Characterization of nicotinic acetylcholine receptor channels of the TE671 human medulloblastoma clonal line," *Neurosci. Lett.* 96: 207-212 (1989).

Rapier, et al., "Nicotinic Modulation of [$^3$H]Dopamine Release from Striatal Synaptosomes: Pharmacological Characterisation," *J. Neurochem.* 54(3): 937-45 (1990).

Ripoll, N. et al., "Nicotinic receptors and schizophrenia," *Current Medical Research and Opinion*, 20(7): 1057-1074 (2004).

Sacco, K.A. et al., "Nicotinic receptor mechanisms and cognition in normal states and neuropsychiatric disorders," *Journal of Psychopharmacology*, 18(4): 457-474 (2004).

Shytle, R.D. et al., "Neuronal Nicotinic Receptor Inhibition for Treating Mood Disorders: Preliminary Controlled Evidence with Mecamylamine," *Depression and Anxiety*, 16: 89-92 (2002).

Shytle, R.D., et al., "Nicotinic acetylcholine receptors as targets for antidepressants," *Molecular Psychiatry*, 7: 525-535 (2002).

Stratton, et al., "Characterization of the human cell line TE671," *Carcinogenesis* 10(5): 899-905 (1989).

Suto, M.J. & Zacharias, N., "Neuronal nicotinic acetylcholine receptors as drug targets," *Expert Opin. Ther. Targets*, 8(2): 61-64 (2004).

Takada, Y. et al., "Nicotinic Acetylcholine Receptor-Mediated Neuroprotection by Donepezil Against Glutamate Neurotoxicity in Rat Cortical Neurons," *The Journal of Pharmacology and Experimental Therapeutics*, 306(2) 772-777 (2003).

Villemagne, V.L. et al., "Nicotine and Related Compounds as PET and SPECT Ligands," *Neuronal Nicotinic Receptors Pharmacology and Therapeutic Opportunities* 235-250 (1998).

Vincler, M., "Neuronal nicotinic receptors as targets for novel analgesics," *Expert Opin. Investig. Drugs*, 14(10: 1191-1198 (2005).

Whiting, P.J., et al., "Functional acetylcholine receptor in PC12 cells reacts with a monoclonal antibody to brain nicotinic receptors," *Nature* 327 515-518 (1987).

Whiting, P.J., et al., "Expression of nicotinic acetylcholine receptor subtypes in brain and retina," *Molecular Brain Research*, 10: 61-70 (1991).

Williams, M., et al., "Neuronal Nicotinic Acetylcholine Receptors," *Drug News Perspec.*, 7(4): 205-223 (1994).

Young, J.M., "Mecamylamine: New Therapeutic Uses and Toxicity/Risk Profile," *Clinical Therapeutics*, 23(4): 532-565 (2001).

International Search Report (PCT/US2008/058384, dated Jul. 7, 2008).

* cited by examiner

SUB-TYPE SELECTIVE AZABICYCLOALKANE DERIVATIVES

CROSS REFERENCE TO RELATED APPLICATION

This application claims priority to PCT Application Number PCT/US2008/058384, filed Mar. 27, 2008, entitled: SUB-TYPE SELECTIVE AZABICYCLOALKANE DERIVATIVES, which claims priority to U.S. Provisional Patent Application Ser. No. 60/909,030, filed Mar. 30, 2007, each of which is herein incorporated by reference in its entirety.

FIELD OF THE INVENTION

The present invention relates to compounds that bind to and modulate the activity of neuronal nicotinic acetylcholine receptors, to processes for preparing these compounds, to pharmaceutical compositions containing these compounds and to methods of using these compounds for treating a wide variety of conditions and disorders, including those associated with dysfunction of the central nervous system (CNS).

BACKGROUND OF THE INVENTION

The therapeutic potential of compounds that target neuronal nicotinic receptors (NNRs), also known as nicotinic acetylcholine receptors (nAChRs), has been the subject of several recent reviews. See, Breining et al., *Ann. Rep. Med. Chem.* 40: 3 (2005), Hogg and Bertrand, *Curr. Drug Targets: CNS Neurol. Disord.* 3:123 (2004), Suto and Zacharias, *Expert Opin. Ther. Targets* 8:61 (2004), Dani et al., *Bioorg. Med. Chem. Lett.* 14: 1837 (2004), Bencherif and Schmitt, *Curr. Drug Targets: CNS Neurol. Disord.* 1: 349 (2002), each of which is incorporated by reference with regard to such teaching. Among the kinds of indications for which NNR ligands have been proposed as therapies are cognitive disorders and dysfunctions, including Alzheimer's disease, attention deficit disorder and schizophrenia. See, Newhouse et al., *Curr. Opin. Pharmacol.* 4: 36 (2004), Levin and Rezvani, *Curr. Drug Targets: CNS Neurol. Disord.* 1: 423 (2002), Graham et al., *Curr. Drug Targets: CNS Neural. Disord.* 1: 387 (2002), Ripoll et al., *Curr. Med. Res. Opin.* 20(7): 1057 (2004), and McEvoy and Allen, *Curr. Drug Targets: CNS Neurol. Disord.* 1: 433 (2002)); pain and inflammation (Decker et al., *Curr. Top. Med. Chem.* 4(3): 369 (2004), Vincler, *Expert Opin. Invest. Drugs* 14(10): 1191 (2005), Jain, *Curr. Opin. Inv. Drugs* 5: 76 (2004), Miao et al., *Neuroscience* 123: 777 (2004)); depression and anxiety (Shytle et al., *Mol. Psychiatry* 7: 525 (2002), Damaj et al., *Mol. Pharmacol.* 66: 675 (2004), Shytle et al., *Depress. Anxiety* 16: 89 (2002)); neurodegeneration (O'Neill et. al., *Curr. Drug Targets: CNS Neurol. Disord.* 1: 399 (2002), Takata et al., *J. Pharmacol. Exp. Ther.* 306: 772 (2003), Marrero et al.,*J. Pharmacol. Exp. Ther.* 309: 16 (2004)); Parkinson's disease (Jonnala and Buccafusco, *J. Neurosci. Res.* 66: 565 (2001)); addiction (Dwoskin and Crooks, *Biochem. Pharmacol.* 63: 89 (2002), Coe et al., *Bioorg. Med. Chem. Lett.* 15(22): 4889 (2005)); obesity (Li et al., *Curr. Top. Med. Chem.* 3: 899 (2003)); and Tourette's syndrome (Sacco et al., *J. Psychopharmacol.* 18(4): 457 (2004), Young et al., *Clin. Ther.* 23(4): 532 (2001); each of which is herein incorporated by reference with regard to such teaching.

A limitation of some nicotinic compounds is that they are associated with various undesirable side effects, for example, by stimulating muscle and ganglionic receptors. It would be desirable to have compounds, compositions and methods for preventing and/or treating various conditions or disorders (e.g., CNS disorders), including alleviating the symptoms of these disorders, where the compounds exhibit nicotinic pharmacology with a beneficial effect (e.g., upon the functioning of the CNS), but without significant associated side effects. It would further be highly desirable to provide compounds, compositions and methods that affect CNS function without significantly affecting those receptor subtypes which have the potential to induce undesirable side effects (e.g., appreciable activity at cardiovascular and skeletal muscle sites). The present invention provides such compounds, compositions, and methods.

SUMMARY OF THE INVENTION

The present invention includes a compound of Formula 1:

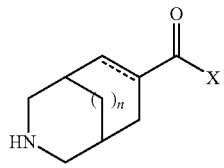

Formula 1 or a pharmaceutically acceptable salt thereof;
wherein the depicted dashed bond indicates either a single or a double bond;
n is 0 or 1;
X is —$OR^I$, —$NR^{II}R^{III}$, —$NR^{II}OR^{III}$, or —$R^{IV}$ when n is 0, and
X is —$NR^{II}R^{III}$, —$NR^{II}OR^{III}$, or —$R^{IV}$ when n is 1;
wherein each of $R^I$ and $R^{IV}$ individually is alkyl, cycloalkyl, substituted alkyl, substituted cycloalkyl, alkenyl, cycloalkenyl, substituted alkenyl, substituted cycloalkenyl, heterocyclyl, substituted heterocyclyl, aryl, heteroaryl, substituted aryl, substituted heteroaryl, arylalkyl, heteroarylalkyl, substituted arylalkyl, or substituted heteroarylalkyl;
each of $R^{II}$ and $R^{III}$ individually is hydrogen, alkyl, cycloalkyl, substituted alkyl, substituted cycloalkyl, alkenyl, cycloalkenyl, substituted alkenyl, substituted cycloalkenyl, heterocyclyl, substituted heterocyclyl, aryl, heteroaryl, substituted aryl, substituted heteroaryl, arylalkyl, heteroarylalkyl, substituted arylalkyl, or substituted heteroarylalkyl;
or $R^{II}$ and $R^{III}$ together can combine with the atoms to which they are attached to form a three- to eight-membered ring;
wherein the term substituted refers to one or more of alkyl, cycloalkyl, alkenyl, cycloalkenyl, heterocyclyl, aryl, heteroaryl, halo, —$OR^I$, —$NR^aR^b$, haloalkyl, —CN, —$NO_2$, —C≡$CR^a$, —$SR^a$, —$N_3$, —C(=O)$NR^aR^b$, —$NR^aC$(=O)$R^b$, —C(=O)$R^a$, —C(=O)$OR^a$, —OC(=O)$R^a$, —OC(=O)$NR^aR^b$, —$NR^aC$(=O)$OR^b$, —$SO_2R^a$, —$SO_2NR^aR^b$, or —$NR^aSO_2R^b$, where each of $R^a$ and $R^b$ individually is hydrogen, alkyl, cycloalkyl, heterocyclyl, aryl, or arylalkyl.

One embodiment of the present invention includes the compounds of the invention in isolated form.

One embodiment of the present invention includes wherein n is 0. A further embodiment includes wherein X is —$OR^I$ and $R^I$ is alkyl, alkyl substituted with halogen, cyclolalkyl, or heterocyclyl, alkenyl, alkynyl, cycloalkyl, cycloalkenyl, heterocyclyl, aryl, or arylalkyl. A further embodiment includes wherein X is —$NR^{II}R^{III}$, $R^{II}$ is hydrogen or alkyl, and $R^{III}$ is hydrogen, alkyl, alkyl substituted with halogen, alkyl substituted with $NH_2$, alkenyl, alkynyl, cycloalkyl, heterocyclyl, aryl, aryl substituted with halogen, heteroaryl, or arylalkyl. A further embodiment includes wherein X is —$NR^{II}OR^{III}$, $R^{II}$ is hydrogen or alkyl, and $R^{III}$ is alkyl. A further embodiment includes wherein X is —$R^{IV}$, and $R^{IV}$ is alkyl, alkyl substituted with halogen, alkenyl, cycloalkyl, heterocyclyl, aryl, aryl substituted with halogen, heteroaryl, or heteroaryl substituted with halogen, cyano, or alkyl.

One embodiment of the present invention includes wherein n is 1. A further embodiment includes wherein X is —$OR^I$ and $R^I$ is alkyl, alkyl substituted with halogen, cyclolakyl, or heterocyclyl, alkenyl, alkynyl, cycloalkyl, cycloalkenyl, heterocyclyl, aryl, or arylalkyl. A further embodiment includes wherein X is —$NR^{II}R^{III}$, $R^{II}$ is hydrogen or alkyl, and $F^{III}$ is hydrogen, alkyl, alkyl substituted with halogen, alkyl substituted with alkoxy, alkyl substituted with $NH_2$, alkenyl, alkynyl, cycloalkyl, aryl, aryl substituted with halogen, heteroaryl, or arylalkyl. A further embodiment includes wherein X is —$R^{IV}$, and $R^{IV}$ is alkyl, alkyl substituted with halogen, alkenyl, cycloalkyl, heterocyclyl, aryl, aryl substituted with halogen, heteroaryl, or heteroaryl substituted with halogen, cyano, or alkyl.

One embodiment of the present invention includes the use of the compound according to the invention in the manufacture of a medicament for treatment of central nervous system disorders.

One embodiment of the present invention includes a method for treatment or prevention of central nervous system disorders, comprising administering a compound of the invention. A further embodiment includes wherein the disorder is selected from the group consisting of age-associated memory impairment, mild cognitive impairment, pre-senile dementia, early onset Alzheimer's disease, senile dementia, dementia of the Alzheimer's type, Lewy body dementia, vascular dementia, Alzheimer's disease, stroke, AIDS dementia complex, attention deficit disorder, attention deficit hyperactivity disorder, dyslexia, schizophrenia, schizophreniform disorder, and schizoaffective disorder.

One embodiment of the present invention includes a pharmaceutical composition a compound of the invention and one or more pharmaceutically acceptable diluent, excipient, or inert carrier. A further embodiment includes a pharmaceutical composition for treatment or prevention of central nervous system disorders.

One embodiment of the present invention includes a compound selected from:
1-(3-azabicyclo[3.3.0]oct-7-yl)-1-ethanone,
1-(3-azabicyclo[3.3.0]oct-7-yl)-2-fluoro-1-ethanone,
1-(3-azabicyclo[3.3.0]oct-7-yl)-2-bromo-1-ethanone,
1-(3-azabicyclo[3.3.0]oct-7-yl)-2-methoxy-1-ethanone,
1-(3-azabicyclo[3.3.0]oct-7-yl)-2-isopropoxy-1-ethanone,
1-(3-azabicyclo[3.3.0]oct-7-yl)-1-propanone,
1-(3-azabicyclo[3.3.0]oct-7-yl)-1-butanone,
trans-1-(3-azabicyclo[3.3.0]oct-7-yl)-2-buten-1-one,
1-(3-azabicyclo[3.3.0]oct-7-yl)-2-methyl-1-propanone,
1-(3-azabicyclo[3.3.0]oct-7-yl)-2,2-dimethyl-1-propanone,
1-(3-azabicyclo[3.3.0]oct-7-yl)-1-pentanone,
1-(3-azabicyclo[3.3.0]oct-7-yl)-2-methyl-1-butanone,
1-(3-azabicyclo[3.3.0]oct-7-yl)-3-methyl-1-butanone,
1-(3-azabicyclo[3.3.0]oct-7-yl)-3,3-dimethyl-1-butanone,
cyclopropyl(3-azabicyclo[3.3.0]oct-7-yl)methanone,
cyclobutyl(3-azabicyclo[3.3.0]oct-7-yl)methanone,
cyclopentyl(3-azabicyclo[3.3.0]oct-7-yl)methanone,
cyclohexyl(3-azabicyclo[3.3.0]oct-7-yl)methanone,
tetrahydropyran-4-yl(3-azabicyclo[3.3.0]oct-7-yl)methanone,
4-fluorophenyl(3-azabicyclo[3.3.0]oct-7-yl)methanone,
furan-2-yl(3-azabicyclo[3.3.0]oct-7-yl)methanone,
furan-2-yl(3-azabicyclo[3.3.0]oct-6-en-7-yl)methanone,
3-bromofuran-2-yl(3-azabicyclo[3.3.0]oct-7-yl)methanone,
3-cyanofuran-2-yl(3-azabicyclo[3.3.0]oct-7-yl)methanone,
5-methyl-2-furanyl(3-azabicyclo[3.3.0]oct-7-yl)methanone,
pyridin-4-yl(3-azabicyclo[3.3.0]oct-7-yl)methanone,
(2-(hydroxymethyl)-1-pyrrolidinyl)(3-azabicyclo[3.3.0]oct-7-yl)methanone,
1-(3-azabicyclo[3.3.1]non-7-yl)-1-ethanone,
1-(3-azabicyclo[3.3.1]non-7-yl)-2-fluoro-1-ethanone,
1-(3-azabicyclo[3.3.1]non-7-yl)-2-bromo-1-ethanone,
1-(3-azabicyclo[3.3.1]non-7-yl)-2-methoxy-1-ethanone,
1-(3-azabicyclo[3.3.1]non-7-yl)-2-isopropoxy-1-ethanone,
1-(3-azabicyclo[3.3.1]non-7-yl)-1-propanone,
1-(3-azabicyclo[3.3.1]non-7-yl)-1-butanone,
trans-1-(3-azabicyclo[3.3.1]non-7-yl)-2-buten-1-one,
1-(3-azabicyclo[3.3.1]non-7-yl)-2-methyl-1-propanone,
1-(3-azabicyclo[3.3.1]non-7-yl)-2,2-dimethyl-1-propanone,
1-(3-azabicyclo[3.3.1]non-7-yl)-1-pentanone,
1-(3-azabicyclo[3.3.1]non-7-yl)-2-methyl-1-butanone,
1-(3-azabicyclo[3.3.1]non-7-yl)-3-methyl-1-butanone,
1-(3-azabicyclo[3.3.1]non-7-yl)-3,3-dimethyl-1-butanone,
cyclopropyl(3-azabicyclo[3.3.1]non-7-yl)methanone,
cyclobutyl(3-azabicyclo[3.3.1]non-7-yl)methanone,
cyclopentyl(3-azabicyclo[3.3.1]non-7-yl)methanone,
cyclohexyl(3-azabicyclo[3.3.1]non-7-yl)methanone,
tetrahydropyran-4-yl(3-azabicyclo[3.3.1]non-7-yl)methanone,
4-fluorophenyl(3-azabicyclo[3.3.1]non-7-yl)methanone,
furan-2-yl(3-azabicyclo[3.3.1]non-7-yl)methanone,
3-bromofuran-2-yl(3-azabicyclo[3.3.1]non-7-yl)methanone,
3-cyanofuran-2-yl(3-azabicyclo[3.3.1]non-7-yl)methanone,
5-methyl-2-furanyl(3-azabicyclo[3.3.1]non-7-yl)methanone,
pyridin-4-yl(3-azabicyclo[3.3.1]non-7-yl)methanone,
methyl 3-azabicyclo[3.3.0]octane-7-carboxylate,
methyl 3-azabicyclo[3.3.0]oct-6-ene-7-carboxylate,
ethyl 3-azabicyclo[3.3.0]octane-7-carboxylate,
isopropyl 3-azabicyclo[3.3.0]octane-7-carboxylate,
2,2-dimethylpropyl 3-azabicyclo[3.3.0]octane-7-carboxylate,
2-fluoroethyl 3-azabicyclo[3.3.0]octane-7-carboxylate,
1-fluoroprop-2-yl 3-azabicyclo[3.3.0]octane-7-carboxylate,
cyclopropylmethyl 3-azabicyclo[3.3.0]octane-7-carboxylate,
cyclobutyl 3-azabicyclo[3.3.0]octane-7-carboxylate,
cyclopentyl 3-azabicyclo[3.3.0]octane-7-carboxylate,
cyclohexyl 3-azabicyclo[3.3.0]octane-7-carboxylate,
pent-4-en-2-yl 3-azabicyclo[3.3.0]octane-7-carboxylate,
pent-4-yn-2-yl 3-azabicyclo[3.3.0]octane-7-carboxylate,
cyclopent-3-en-1-yl 3-azabicyclo[3.3.0]octane-7-carboxylate,
(tetrahydrofuran-3-yl)methyl 3-azabicyclo[3.3.0]octane-7-carboxylate,
tetrahydrofuran-3-yl 3-azabicyclo[3.3.0]octane-7-carboxylate,
tetrahydropyran-4-yl 3-azabicyclo[3.3.0]octane-7-carboxylate,
(furan-3-yl)methyl 3-azabicyclo[3.3.0]octane-7-carboxylate,
benzyl 3-azabicyclo[3.3.0]octane-7-carboxylate,
3-azabicyclo[3.3.0]octane-7-carboxamide,
N-allyl-3-azabicyclo[3.3.0]octane-7-carboxamide,
N-(2-furanylmethyl)-3-azabicyclo[3.3.0]octane-7-carboxamide,
N-methyl-3-azabicyclo[3.3.0]octane-7-carboxamide, N-ethyl-3-azabicyclo[3.3.0]octane-7-carboxamide,
N-(2-methoxyethyl)-3-azabicyclo[3.3.0]octane-7-carboxamide,
N,N-dimethyl-3-azabicyclo[3.3.0]octane-7-carboxamide,
N,N-dimethyl-3-azabicyclo[3.3.0]oct-6-ene-7-carboxamide,
N-isopropyl-3-azabicyclo[3.3.0]octane-7-carboxamide,
N-cyclopropyl-3-azabicyclo[3.3.0]octane-7-carboxamide,
N-cyclobutyl-3-azabicyclo[3.3.0]octane-7-carboxamide,
N-cyclopentyl-3-azabicyclo[3.3.0]octane-7-carboxamide,
N-methyl-N-methoxy-3-azabicyclo[3.3.0]octane-7-carboxamide,
N-methyl-N-methoxy-3-azabicyclo[3.3.0]oct-6-ene-7-carboxamide,
N-methyl-N-propargyl-3-azabicyclo[3.3.0]octane-7-carboxamide,
N-phenyl-3-azabicyclo[3.3.0]octane-7-carboxamide,
N-(4-fluorophenyl)-3-azabicyclo[3.3.0]octane-7-carboxamide,
N-(pyridin-3-yl)-3-azabicyclo[3.3.0]octane-7-carboxamide,
N-benzyl-3-azabicyclo[3.3.0]octane-7-carboxamide,
(3-azabicyclo[3.3.0]oct-7-yl)(2,3,6-trihydro-pyridin-1-yl)methanone,
(3-azabicyclo[3.3.0]oct-7-yl)(2,6-methyl-morpholin-1-yl)methanone,
(3-azabicyclo[3.3.0]oct-6-en-7-yl)(2,6-dimethylmorpholin-1-yl)methanone
(3-azabicyclo[3.3.0]oct-7-yl)(1-oxazinan-2-yl)methanone,
3-azabicyclo[3.3.1]nonane-7-carboxamide,
N-methyl-3-azabicyclo[3.3.1]nonane-7-carboxamide,
N-ethyl-3-azabicyclo[3.3.1]nonane-7-carboxamide,
N-(2-methoxyethyl)-3-azabicyclo[3.3.1]nonane-7-carboxamide,
N,N-dimethyl-3-azabicyclo[3.3.1]nonane-7-carboxamide,
N-isopropyl-3-azabicyclo[3.3.1]nonane-7-carboxamide,
N-cyclopropyl-3-azabicyclo[3.3.1]nonane-7-carboxamide,
N-cyclobutyl-3-azabicyclo[3.3.1]nonane-7-carboxamide,
N-cyclopentyl-3-azabicyclo[3.3.1]nonane-7-carboxamide,
N-methyl-N-methoxy-3-azabicyclo[3.3.1]nonane-7-carboxamide,
N-methyl-N-propargyl-3-azabicyclo[3.3.1]nonane-7-carboxamide,
N-phenyl-3-azabicyclo[3.3.1]nonane-7-carboxamide,
N-(4-fluorophenyl)-3-azabicyclo[3.3.1]nonane-7-carboxamide,
N-(pyridin-3-yl)-3-azabicyclo[3.3.1]nonane-7-carboxamide,
N-benzyl-3-azabicyclo[3.3.1]nonane-7-carboxamide,
N-(2-aminoethyl)-3-azabicyclo[3.3.1]nonane-7-carboxamide,
N-tert-butyl-3-azabicyclo[3.3.1]nonane-7-carboxamide,
N-propyl-3-azabicyclo[3.3.1]nonane-7-carboxamide,
N-allyl-3-azabicyclo[3.3.1]nonane-7-carboxamide,
N-(2-fluorophenyl)-3-azabicyclo[3.3.1]nonane-7-carboxamide,
N-sec-butyl-3-azabicyclo[3.3.1]nonane-7-carboxamide,
N-(cyclopropylmethyl)-3-azabicyclo[3.3.1]nonane-7-carboxamide,
N-(2-fluoroethyl)-3-azabicyclo[3.3.1]nonane-7-carboxamide,
N-(2,2,2-trifluoroethyl)-3-azabicyclo[3.3.1]nonane-7-carboxamide,
N-(3-fluoropropyl)-3-azabicyclo[3.3.1]nonane-7-carboxamide,
N-(3-cyclopentenyl)-3-azabicyclo[3.3.1]nonane-7-carboxamide,
(3-azabicyclo[3.3.1]non-7-yl)(2,3,6-trihydro-pyridin-1-yl)methanone,
(3-azabicyclo[3.3.1]non-7-yl)(2,6-methyl-morpholin-1-yl)methanone,
(3-azabicyclo[3.3.1]non-7-yl)(1-oxazinan-2-yl)methanone,
4-morpholinyl(3-azabicyclo[3.3.1]non-7-yl)methanone,
or a pharmaceutically acceptable salt thereof.

One embodiment of the present invention includes a compound selected as described in isolated form.

One embodiment of the present invention includes a method for treatment or prevention of central nervous system disorders, comprising administering a as selected. One embodiment of the present invention includes a method for treatment or prevention of central nervous system disorders, comprising administering a salt of a compound as selected. In such embodiments, a further embodiment includes wherein the disorder is selected from the group consisting of age-associated memory impairment, mild cognitive impairment, pre-senile dementia, early onset Alzheimer's disease, senile dementia, dementia of the Alzheimer's type, Lewy body dementia, vascular dementia, Alzheimer's disease, stroke, AIDS dementia complex, attention deficit disorder, attention deficit hyperactivity disorder, dyslexia, schizophrenia, cognitive deficits in schizophrenia, cognitive dysfunction in schizophrenia, schizophreniform disorder, and schizoaffective disorder. In a further embodiment, the disorder is selected from the group consisting of mild to moderate dementia of the Alzheimer's type, attention deficit disorder, mild cognitive impairment, and age associated memory impairment.

One embodiment of the present invention includes a compound, methyl 3-azabicyclo[3.3.0]octane-7-carboxylate, as a pharmaceutically acceptable salt.

One embodiment of the present invention includes a compound, N-methyl-3-azabicyclo[3.3.1]nonane-7-carboxamide or a pharmaceutically acceptable salt thereof.

The present invention includes all combinations of aspects and embodiments.

The present invention relates to amide compounds which can be formed from certain heteroarylcarboxylic acids and certain diazabicycloalkanes. These amide compounds (heteroarylcarboxamides) bind with high affinity to neuronal nicotinic receptors of the α4β2 subtype, found in the central nervous system (CNS), and exhibit selectivity for the α4β2 subtype over the α7 NNR subtype, also found in the CNS.

The present invention also relates to pharmaceutically acceptable salts prepared from these amide compounds and the pharmaceutical compositions thereof, which can be used for treating and/or preventing a wide variety of conditions or disorders, and particularly those disorders characterized by dysfunction of nicotinic cholinergic neurotransmission or the degeneration of the nicotinic cholinergic neurons.

The present invention also relates to methods for treating or preventing disorders, such as CNS disorders and also for treating certain conditions, namely, alleviating pain and inflammation. The methods involve administering to a subject a therapeutically effective amount of the compounds, including salts, or pharmaceutical compositions including such compounds. Further provided is a method for treatment of disorders selected from the group consisting of age-associated memory impairment, mild cognitive impairment, pre-senile dementia, early onset Alzheimer's disease, senile dementia, dementia of the Alzheimer's type, Lewy body dementia, vascular dementia, Alzheimer's disease, stroke, AIDS dementia complex, attention deficit disorder, attention deficit hyperactivity disorder, dyslexia, schizophrenia, cognitive dysfunction in schizophrenia, schizophreniform disorder, and schizoaffective disorder. Even further provided is a method for treatment of disorders selected from the group consisting of the treatment of mild to moderate dementia of the Alzheimer's type, attention deficit disorder, mild cognitive impairment, age associated memory impairment, and cognitive dysfunction in schizophrenia.

The pharmaceutical compositions incorporate a compound of the present invention which, when employed in effective amounts, interacts with relevant nicotinic receptor sites of a subject, and hence acts as a therapeutic agent to treat and prevent a wide variety of conditions and disorders. The pharmaceutical compositions provide therapeutic benefit to individuals suffering from such disorders and exhibiting clinical manifestations of such disorders, in that the compounds within those compositions, when employed in effective amounts, can (i) exhibit nicotinic pharmacology and affect relevant nicotinic receptors sites (e.g., act as a pharmacological agonist to activate nicotinic receptors), and/or (ii) elicit neurotransmitter secretion, and hence prevent and suppress the symptoms associated with those diseases. In addition, the compounds have the potential to (i) increase the number of nicotinic cholinergic receptors of the brain of the patient, (ii) exhibit neuroprotective effects, and/or (iii) when employed in effective amounts, to not cause appreciable adverse side effects (e.g., significant increases in blood pressure and heart rate, significant negative effects upon the gastro-intestinal tract, and significant effects upon skeletal muscle).

The foregoing and other aspects of the present invention are explained in detail in the detailed description and examples set forth below.

DETAILED DESCRIPTION

Figure 1:
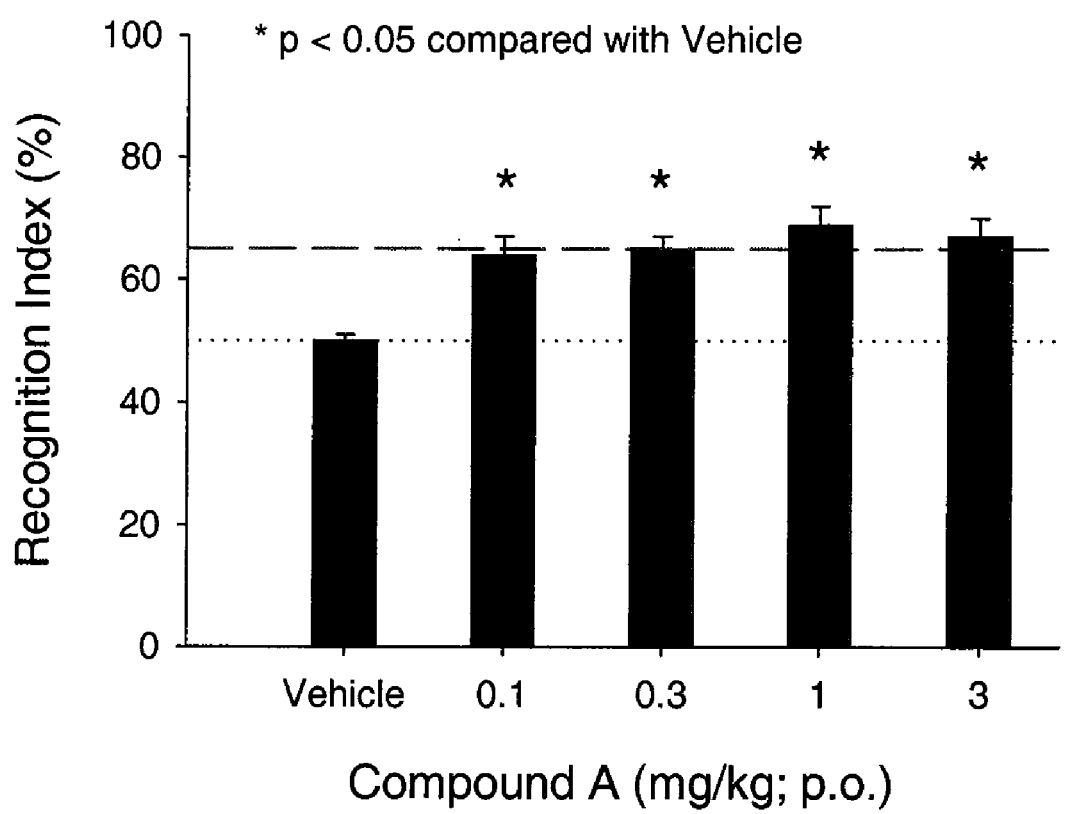
FIG. 1 is a chart showing the results of a study on novel object recognition in rats treated orally with Compound A, methyl 3-azabicyclo[3.3.0]octane-7-carboxylate. The results are shown as a function of recognition index (%) versus dose (mg/kg).

The subtype selective compounds, pharmaceutical compositions including these compounds, methods of preparing the compounds, and methods of treatment and/or prevention using the compounds are described in detail below.

The following definitions are meant to clarify, but not limit, the terms defined. If a particular term used herein is not specifically defined, such term should not be considered indefinite. Rather, terms are used within their accepted meanings.

As used herein the term "alkyl" refers to a straight or branched chain hydrocarbon having one to twelve carbon atoms, preferably one to six, which may be optionally substituted as herein further described, with multiple degrees of substitution being allowed. Examples of "alkyl" as used herein include, but are not limited to, methyl, ethyl, propyl, isopropyl, isobutyl, n-butyl, tert-butyl, isopentyl, and n-pentyl.

As used throughout this specification, the preferred number of atoms, such as carbon atoms, will be represented by, for example, the phrase "$C_x$-$C_y$ alkyl," which refers to an alkyl group, as herein defined, containing the specified number of carbon atoms. Similar terminology will apply for other preferred terms and ranges as well. One embodiment of the present invention includes so-called 'lower' alkyl chains of one to six carbon atoms. Thus, $C_1$-$C_6$ alkyl represents a lower alkyl chain as hereinabove described.

As used herein the term "alkenyl" refers to a straight or branched chain aliphatic hydrocarbon having two to twelve carbon atoms, preferably two to six, and containing one or more carbon-to-carbon double bonds, which may be optionally substituted as herein further described, with multiple degrees of substitution being allowed. Examples of "alkenyl" as used herein include, but are not limited to, ethenyl, propenyl, butenyl, and the like.

As used herein the term "alkynyl" refers to a straight or branched chain aliphatic hydrocarbon having two to twelve carbon atoms, preferably two to six, and containing one or more carbon-to-carbon triple bonds, which may be optionally substituted as herein further described, with multiple degrees of substitution being allowed. Examples of "alkynyl" as used herein include, but are not limited to, vinyl, allyl, and propargyl.

As used herein, the term "cycloalkyl" refers to a partially or fully saturated, optionally substituted, non-aromatic, three- to twelve-membered, monocyclic, bicyclic, or bridged hydrocarbon ring, with multiple degrees of substitution being allowed. Exemplary "cycloalkyl" groups as used herein include, but are not limited to, cyclopropyl, cyclobutyl, cyclopentyl, cyclohexyl, cycloheptyl, and cyclooctyl, as well as rings containing one or more degrees of unsaturation but short of aromatic, such as cyclopropenyl, cyclobutenyl, cyclopentenyl, cyclohexenyl, and cycloheptenyl.

As used herein, the term "heterocycle" or "heterocyclyl" refers to an optionally substituted mono- or polycyclic ring system, optionally containing one or more degrees of unsaturation and also containing one or more heteroatoms, which may be optionally substituted as herein further described, with multiple degrees of substitution being allowed. Exemplary heteroatoms include nitrogen, oxygen, or sulfur atoms, including N-oxides, sulfur oxides, and dioxides. Preferably, the ring is three to twelve-membered and is either fully saturated or has one or more degrees of unsaturation. Such rings may be optionally fused to one or more of another heterocyclic ring(s) or cycloalkyl ring(s). Examples of "heterocyclic" groups as used herein include, but are not limited to, tetrahydrofuranyl, pyranyl, tetrahydropyranyl, 1,4-dioxanyl, 1,3-dioxanyl, piperidinyl, pyrrolidinyl, morpholinyl, oxazinanyl, piperizinyl, tetrahydrothiopyranyl, and tetrahydrothiophenyl.

As used herein, the term "aryl" refers to a univalent benzene ring or fused benzene ring system, which may be optionally substituted as herein further described, with multiple degrees of substitution being allowed. Examples of "aryl" groups as used include, but are not limited to, phenyl, 2-naphthyl, 1-naphthyl, anthracene, and phenanthrene. Preferably, aryl is phenyl or naphthyl.

As used herein, a fused benzene ring system encompassed within the term "aryl" includes fused polycyclic hydrocarbons, namely where a cyclic hydrocarbon with less than maximum number of noncumulative double bonds, for example where a saturated hydrocarbon ring (cycloalkyl, such as a cyclopentyl ring) is fused with an aromatic ring (aryl, such as a benzene ring) to form, for example, groups such as indanyl and acenaphthalenyl, and also includes such groups as, for non-limiting examples, dihydronaphthalene and hexahydrocyclopenta-cyclooctene.

As used herein, the term "arylalkyl" refers to an "aryl" group as herein defined attached through a divalent alkylene linker. As one example, the term includes benzyl.

As used herein, the term "heteroaryl" refers to a monocyclic five to seven membered aromatic ring, or to a fused bicyclic aromatic ring system comprising two of such aromatic rings, which may be optionally substituted as herein further described, with multiple degrees of substitution being allowed. These heteroaryl rings contain one or more nitrogen, sulfur, and/or oxygen atoms, where N-oxides, sulfur oxides, and dioxides are permissible heteroatom substitutions. Examples of "heteroaryl" groups as used herein include, but should not be limited to, furanyl, thiophenyl or thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzodioxolyl, benzothiophenyl, indolyl, indolinyl, indazole, benzimidizolyl, indolizinyl, imidazopyridinyl, purinyl, pyrazolopyridinyl, and pyrazolopyrimidinyl.

In this specification, unless stated otherwise, the terms "halo" and "halogen" may be fluorine, iodine, chlorine, or bromine.

As will be appreciated throughout the specification, the number and nature of substituents on rings in the compounds of the invention will be selected so as to avoid sterically undesirable combinations.

Certain compound names of the present invention were generated with the aid of computer software (ACDLabs 8.0/Name(IUPAC)).

Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates. Representative salts are provided as described in U.S. Pat. No. 5,597,919 to Dull et al., U.S. Pat. No. 5,616,716 to Dull et al. and U.S. Pat. No. 5,663,356 to Ruecroft et al.

As will be appreciated by those skilled in the art, the compounds of the present invention may exist in solvated, for example hydrated, as well as unsolvated forms. Further, the compounds may exist as co-crystals. The present invention encompasses all such forms.

For the avoidance of doubt, the present invention relates to any salts of forms as mentioned above, and explicitly for any one of the specific compounds mentioned herein in the form of any one of the salts mentioned hereinabove. Additionally, as noted, the present invention includes solvates of the compounds herein described, including combinations, such as solvates of a salt. As noted, the compounds of the present invention may exist in solvated, for example hydrated, as well as unsolvated forms, and the present invention encompasses all such forms.

As herein described, the present invention includes a compound of the present invention in isolated form. As used herein, the phrase "in isolated form" provides for the compound to be substantially free from other compounds, including by-products, impurities, and synthetic reagents. As used herein, the phrase "substantially free" should be interpreted to be approximately 95% free from such described other components.

As used herein, an "agonist" is a substance that stimulates its binding partner, typically a receptor. Stimulation is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Stimulation may be defined with respect to an increase in a particular effect or function that is induced by interaction of the agonist or partial agonist with a binding partner and can include allosteric effects.

As used herein, an "antagonist" is a substance that inhibits its binding partner, typically a receptor. Inhibition is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Inhibition may be defined with respect to a decrease in a particular effect or function that is induced by interaction of the antagonist with a binding partner, and can include allosteric effects.

As used herein, a "partial agonist" is a substance that provides a level of stimulation to its binding partner that is intermediate between that of a full or complete antagonist and an agonist defined by any accepted standard for agonist activity. It will be recognized that stimulation, and hence, inhibition is defined intrinsically for any substance or category of substances to be defined as agonists, antagonists, or partial agonists.

As used herein, "intrinsic activity" or "efficacy" relates to some measure of biological effectiveness of the binding partner complex. With regard to receptor pharmacology, the context in which intrinsic activity or efficacy should be defined will depend on the context of the binding partner (e.g., receptor/ligand) complex and the consideration of an activity relevant to a particular biological outcome. For example, in some circumstances, intrinsic activity may vary depending on the particular second messenger system involved. See Hoyer, D. and Boddeke, H., *Trends Pharmacol. Sci.* 14(7): 270-5 (1993). Where such contextually specific evaluations are relevant, and how they might be relevant in the context of the present invention, will be apparent to one of ordinary skill in the art.

As used herein, modulation of a receptor includes agonism, partial agonism, antagonism, partial antagonism, or inverse agonism of a receptor.

As used herein, neurotransmitters whose release is mediated by the compounds described herein include, but are not limited to, acetylcholine, dopamine, norepinephrine, serotonin and glutamate, and the compounds described herein function as modulators at the α4β2 subtype of the CNS NNRs.

As will be appreciated by those skilled in the art, compounds of the present invention are chiral. The present invention includes all stereoisomeric forms (e.g., enantiomeric or diastereomeric forms) of such compounds and mixtures thereof. Thus, the scope of the present invention includes mixtures of stereoisomers as well as purified enantiomers or enantiomerically/diastereomerically enriched mixtures. Also included within the scope of the invention are the individual isomers of the compounds represented by the formulae of the present invention, as well as any wholly or partially equilibrated mixtures thereof. The present invention also includes the individual isomers of the compounds represented by the formulas above as mixtures with isomers thereof in which one or more chiral centers are inverted.

Representative compounds of the present invention include those that are specifically exemplified and identified. For the avoidance of doubt, the present invention relates to any one of the specific compounds herein described.

Compound Preparation

The compounds of the present invention can be prepared using a variety of synthetic methodologies. Conveniently, they can be prepared via the derivatization of a protected azabicyclic carboxylic acid (i.e., one in which the amine functional group is rendered un-reactive by suitable derivatization). There are numerous methods for the preparation of the azabicyclic carboxylic acids used in the preparation of compounds of the present invention.

Methods for the synthesis of suitable 3-azabicyclo[3.3.0] octane intermediates vary. For instance, Flynn et al., *Tetrahedron* 53(1): 1-20 (1996), provides two approaches to suitably functionalized 3-azabicyclo[3.3.0]octanes. Such reference is herein incorporated by reference with regard to such synthetic teaching. The first approach involves the palladium-catalyzed [3+2] cycloaddition reaction of 2-trimethylsilylmethyl-2-propen-1-yl acetate with dimethyl maleate. The resulting diester is saponified, treated with acetic anhydride, and pyrolyzed to give the fused cyclic anhydride, tetrahydro-5-methylene-1H-cyclopenta[c]furan-1,3(3aH)-dione. Treatment with ammonia followed by cyclization with acetyl chloride gives the imide, tetrahydro-5-methylene-1H-cyclopenta[c] pyrrole-1,3(2H,2aH)-dione. Reduction with lithium aluminum hydride and protection of the free amine with di-tert-butyl dicarbonate gives 7-methylene-3-(tert-butoxycarbonyl)-3-azabicyclo[3.3.0]octane. Subsequent transformations, using this methylene compound, are possible. For instance, ozonolysis of 7-methylene-3-(tert-butoxycarbonyl)-3-azabicyclo[3.3.0]octane will give 3-(tert-butoxycarbonyl)-3-azabicyclo[3.3.0]octan-7-one. Alternately, treatment of 7-methylene-3-(tert-butoxycarbonyl)-3-azabicyclo[3.3.0]octane with borane, followed by aqueous basic hydrogen peroxide, will produce 7-(hydroxymethyl)-3-(tert-butoxycarbonyl)-3-azabicyclo[3.3.0] octane. Oxidation of this alcohol by any number of methods, known to those of skill in the art of organic synthesis, will generate 3-(tert-butoxycarbonyl)-3-azabicyclo[3.3.0]octane-7-carboxylic acid, a key intermediate for the synthesis of compounds of the present invention.

In a second approach, Flynn et al. (*Tetrahedron* 53(1): 1-20 (1996)), uses a Pauson-Khand protocol for generating a suitably functionalized 3-azabicyclo[3.3.0]octane. Such reference is herein incorporated by reference with regard to such synthetic teaching. With this approach, the cyclization of a N-boc-allylpropargylaminehexacarbonyldicobalt complex (Becker and Flynn, *Tetrahedron* 49: 5047-5054 (1993)), gives the aforementioned 3-(tert-butoxycarbonyl)-3-azabicyclo[3.3.0]octan-7-one in one step. Such reference is herein incorporated by reference with regard to such synthetic teaching. Subsequent conversion of the ketone to its enol triflate (using, for instance, lithium hexamethyldisilazide and N-(5-chloropyridin-2-yl)-bis-trifluoromethanesulfinamide), followed by palladium-catalyzed carbomethoxylation (Peterson et al., *J. Med. Chem.* 37: 275-286 (1994), for example), will give methyl 3-(tert-butoxycarbonyl)-3-azabicyclo[3.3.0]oct-6-ene-7-carboxylate. Such reference is herein incorporated by reference with regard to such synthetic teaching. This can be further transformed into key intermediates for synthesis of compounds of the present invention. For instance, hydrogenation will produce the corresponding alkane, methyl 3-(tert-butoxycarbonyl)-3-azabicyclo[3.3.0]octane-7-carboxylate. Removal of the tert-butoxycarbonyl protecting group (acidic conditions) then gives methyl 3-azabicyclo[3.3.0]octane-7-carboxylate. Alternately, methyl 3-(tert-butoxycarbonyl)-3-azabicyclo[3.3.0]oct-6-ene-7-carboxylate can be hydrolyzed, in mild aqueous base, to give the corresponding carboxylic acid, 3-(tert-butoxycarbonyl)-3-azabicyclo[3.3.0] oct-6-ene-7-carboxylic acid, another key intermediate for synthesis of compounds of the present invention.

Another approach to construction of 3-(tert-butoxycarbonyl)-3-azabicyclo[3.3.0]octan-7-one is reported in PCT WO 04/016604 to Dart et al. Such reference is herein incorporated by reference with regard to such synthetic teaching. In this approach, cis-tetrahydrophthalimide is reduced to the corresponding amine with lithium aluminum hydride, and the amine is subsequently protected by reaction with di-tert-butyl dicarbonate. The alkene is then oxidatively cleaved (sodium periodate and catalytic ruthenium(IV) oxide hydrate) to give cis-1-(tert-butoxycarbonyl)-3,4-bis(carboxymethyl)pyrrolidine. Heating with acetic anhydride and sodium acetate gives 3-(tert-butoxycarbonyl)-3-azabicyclo[3.3.0]octan-7-one.

Methods for construction of 3-azabicyclo[3.3.0]octanes can vary. Another route to 3-(tert-butoxycarbonyl)-3-azabicyclo[3.3.0]octane-7-carboxylic acid is described by Flynn and Zabrowski, *J. Org. Chem.* 55: 3673-3674 (1990) and in Flynn et al. in *Tetrahedron Lett.*, 33(48): 7281-82 (1992). Such references are herein incorporated by reference with regard to such synthetic teaching. In this route, diethyl allylmalonate is first iodinated to give diethyl 2-iodo-2-allylmalonate. Subsequent reaction of the malonate with N-(tert-butoxycarbonyl)allylamine and bis(tributyltin), followed by heating in triethylamine, gives diethyl 3-(tert-butoxycarbonyl)-3-azabicyclo[3.3.0]octane-7,7-dicarboxylate. Acidic hydrolysis, with spontaneous decarboxylation, and subsequent re-protection of the amine with di-tert-butyl dicarbonate, gives 3-(tert-butoxycarbonyl)-3-azabicyclo[3.3.0]octane-7-carboxylic acid, a key intermediate for synthesis of compounds of the present invention.

Another alkene cyclization route to 3-azabicyclo[3.3.0] octanes is described by Minakata et al., in *Heterocycles*, 60: 289-98 (2003), in which a tandem cyclization of diethyl 2,2-diallylmalonate is accomplished, using chloramine-T and silver nitrate. Such reference is herein incorporated by reference with regard to such synthetic teaching. The resulting diethyl 3-tosyl-3-azabicyclo[3.3.0]octane-7,7-dicarboxylate can be hydrolyzed in aqueous acid to give 3-tosyl-3-azabicyclo [3.3.0]octane-7-carboxylic acid, which could be used to make compounds of the present invention.

Methods for the synthesis of 3-azabicyclo[3.3.1]nonane derivatives, suitable for making compounds of the present invention, can vary. Speckamp et al., *Tetrahedron* 27: 3143-56 (1971) and Stetter and Reinartz, *Chem. Ber.* 105(9): 2773-2779 (1972) describe the condensation of various N-protected-4-piperidone pyrrolidine enamines with either ethyl α-bromomethacrylate or the corresponding β,β'-dibromoisobutyrate, to give ethyl N-protected-3-aza-9-oxo-bicyclo[3.3.1]nonane-7-carboxylates. Such references are herein incorporated by reference with regard to such synthetic teaching. Subsequent deoxygenation of the 9-position carbonyl, through the intermediacy of the corresponding hydrazones or substituted hydrazones (methods known to those of skill in the art of organic synthesis), gives ethyl N-protected-3-azabicyclo[3.3.1]nonane-7-carboxylates. Hydrolysis of the ester gives N-protected-3-azabicyclo[3.3.1]nonane-7-carboxylic acids, key intermediates for synthesis of compounds of the present invention.

Methods for installation and removal of the tert-butoxycarbonyl and other amine protecting groups will be well known by those skilled in the art and are described further in T. W. Greene and P. G. M. Wuts, Protective Groups in Organic Synthesis, 3$^{rd}$ Edition, John Wiley & Sons, New York (1999), with such reference herein incorporated by reference with regard to such synthetic teaching.

Conversion of the azabicyclic carboxylic acids into compounds of the present invention can be accomplished by a variety of means, all familiar to those skilled in the art of organic synthesis. Thus, N-protected 3-azabicyclo[3.3.0]octane-7-carboxylic acids with acid-stable N-protecting groups can be converted directly into the corresponding esters by reaction with the alcohol in the presence of a strong acid. Alternately, the N-protected 3-azabicyclo[3.3.0]octane-7-carboxylic acid can be reacted with the alcohol in the presence of a coupling (dehydrating) reagent, such as dicyclohexycarbodiimide (DCC), to produce the corresponding ester. This latter reaction can be utilized with acid-sensitive N-protecting groups present. Other ester syntheses, such as those utilizing the corresponding acid chloride or a sulfonic-mixed anhydride as intermediate, are known to those of skill in the art. Many of these reactions also are applicable to the conversion of azabicycloalkene carboxylic acids into esters.

Methods for converting the azabicyclic carboxylic acids into the corresponding amides are also numerous. For instance, the N-protected 3-azabicyclo[3.3.0]octane-7-carboxylic acids and the N-protected 3-azabicyclo[3.3.1]nonane-7-carboxylic acids can be directly coupled with a variety of amines using coupling agents, such as those developed for peptide synthesis. Such reagents include N,N'-dicyclohexylcarbodiimide (DCC), (benzotriazol-1-yloxy)tris(dimethylamino)phosphonium hexafluorophosphate (BOP), (benzotriazol-1-yloxy)tripyrrolidinophosphonium hexafluorophosphate (PyBOP), O-(benzotriazol-1-yl)-N,N,N',N'-bis(tetramethylene)uronium hexafluorophosphate (HBPyU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), and (1-ethyl-3-(3-dimethylaminopropyl)carbodiimide) (EDCI) with 1-hydroxybenzotriazole (HOBt). Other coupling agents are well known to those skilled in the art (for example, see Kiso and Yajima, Peptides, pp 39-91, Academic Press, San Diego, Calif. (1995)). Such reference is herein incorporated by reference with regard to such synthetic teaching. In some cases these reagents are commercially available as polymer supported modifications, which greatly facilitate isolation of coupling products. An example of such a reagent is polystyrene bound N,N'-dicyclohexylcarbodiimide (PS-DCC).

Methods for converting the azabicyclic carboxylic acids into the corresponding amides can vary. Thus, suitable protected azabicycloalkane carboxylic acids can be converted into their corresponding acid chlorides (using, for instance, oxalyl chloride). Reaction of the acid chloride with a primary or secondary amine, in the presence of a suitable base (often a tertiary amine), will produce the amide. This and many of the foregoing reactions are also applicable to the conversion of azabicycloalkene carboxylic acids into amides.

Methods for converting the azabicyclic carboxylic acids into the corresponding ketones are numerous. Thus, the N-protected 3-azabicyclo[3.3.0]octane-7-carboxylic acids and the N-protected 3-azabicyclo[3.3.1]nonane-7-carboxylic acids can be converted to the ketone derivatives through the intermediacy of acid chlorides (already described), in which the acid chloride is reacted with a lithium dialkylcuprate or a dialkylcadmium reagent. Alternately, the carboxylic acid can be converted into its N-methyl-N-methoxy amide (as described above), which readily reacts with organolithium reagents and Grignard reagents to give ketones. Many of the fore-going reactions are also applicable to the conversion of azabicycloalkene carboxylic acids into amides. Certain ketones can also be produced by reaction of acid chlorides with trimethylsilyldiazomethane. This produces the corresponding α-diazoketones, which can be converted into a variety of derivatives (e.g., α-bromoketones).

Those skilled in the art of organic synthesis will appreciate that there exist multiple means of producing compounds of the present invention which are labeled with a radioisotope appropriate to various diagnostic uses. For instance, condensation of a $^{11}$C-amine with either N-(tert-butoxycarbonyl)-3-azabicyclo[3.3.0]octane-7-carboxylic acid chloride or N-(tert-butoxycarbonyl)-3-azabicyclo[3.3.1]nonane-7-carboxylic acid chloride, using the methods described above, and subsequent removal of the tert-butoxycarbonyl group, will produce a compound suitable for use in positron emission tomography.

Methods of Treatment

As used herein, the terms "prevention" or "prophylaxis" include any degree of reducing the progression of or delaying the onset of a disease, disorder, or condition. The term includes providing protective effects against a particular disease, disorder, or condition as well as amelioration of the recurrence of the disease, disorder, or condition. Thus, in another aspect, the invention provides a method for treating a subject having or at risk of developing or experiencing a recurrence of a NNR or nAChR mediated disorder. The compounds and pharmaceutical compositions of the invention may be used to achieve a beneficial therapeutic or prophylactic effect, for example, in a subject with a CNS dysfunction.

As noted above, the compounds of the present invention are modulators of the α4β2 NNR subtype, characteristic of the CNS, and can be used for preventing or treating various conditions or disorders, including those of the CNS, in subjects which have or are susceptible to such conditions or disorders, by modulation of α4β2 NNRs. The compounds have the ability to selectively bind to the α4β2 NNRs and express nicotinic pharmacology, for example, to act as agonists, partial agonists, antagonists, as described. For example, compounds of the present invention, when administered in effective amounts to patients in need thereof, provide some degree of prevention of the progression of the CNS disorder, namely, providing protective effects, amelioration of the symptoms of the CNS disorder, or amelioration of the reoccurrence of the CNS disorder, or a combination thereof.

The compounds of the present invention can be used to treat or prevent those types of conditions and disorders for which other types of nicotinic compounds have been proposed or are shown to be useful as therapeutics. See, for example, the references previously listed hereinabove, as well as Williams et al., *Drug News Perspec.* 7(4): 205 (1994), Arneric et al., *CNS Drug Rev.* 1(1): 1-26 (1995), Arneric et al., *Exp. Opin. Invest. Drugs* 5(1): 79-100 (1996), Bencherif et at, *J. Pharmacol Exp. Ther.* 279: 1413 (1996), Lippiello et al., *J. Pharmacol. Exp. Ther.* 279: 1422 (1996), Damaj et al., *J. Pharmacol. Exp. Ther.* 291: 390 (1999); Chiari et al., *Anesthesiology* 91: 1447 (1999), Lavand'homme and Eisenbach, *Anesthesiology* 91: 1455 (1999), Holladay et al., *J. Med. Chem.* 40(28): 4169-94 (1997), Bannon et al., *Science* 279: 77 (1998), PCT WO 94/08992, PCT WO 96/31475, PCT WO 96/40682, and U.S. Pat. No. 5,583,140 to Bencherif et al., U.S. Pat. No. 5,597,919 to Dull et al., U.S. Pat. No. 5,604,231 to Smith et al. and U.S. Pat. No. 5,852,041 to Cosford et al., the disclosures of which are incorporated herein by reference with regard to such therapeutic teaching.

The compounds and their pharmaceutical compositions are useful in the treatment or prevention of a variety of CNS disorders, including neurodegenerative disorders, neuropsychiatric disorders, neurologic disorders, and addictions. The compounds and their pharmaceutical compositions can be used to treat or prevent cognitive deficits and dysfunctions, age-related and otherwise; attentional disorders and dementias, including those due to infectious agents or metabolic disturbances; to provide neuroprotection; to treat convulsions and multiple cerebral infarcts; to treat mood disorders, compulsions and addictive behaviors; to provide analgesia; to control inflammation, such as mediated by cytokines and nuclear factor kappa B; to treat inflammatory disorders; to provide pain relief; and to treat infections, as anti-infectious agents for treating bacterial, fungal, and viral infections. Among the disorders, diseases and conditions that the compounds and pharmaceutical compositions of the present invention can be used to treat or prevent are: age-associated memory impairment (AAMI), mild cognitive impairment (MCI), age-related cognitive decline (ARCD), pre-senile dementia, early onset Alzheimer's disease, senile dementia, dementia of the Alzheimer's type, Alzheimer's disease, cognitive impairment no dementia (CIND), Lewy body dementia, HIV-dementia, AIDS dementia complex, vascular dementia, Down syndrome, head trauma, traumatic brain injury (TBI), dementia pugilistica, Creutzfeld-Jacob Disease and prion diseases, stroke, ischemia, attention deficit disorder, attention deficit hyperactivity disorder, dyslexia, schizophrenia, schizophreniform disorder, schizoaffective disorder, cognitive dysfunction in schizophrenia, cognitive deficits in schizophrenia, Parkinsonism including Parkinson's disease, postencephalitic parkinsonism, parkinsonism-dementia of Gaum, frontotemporal dementia Parkinson's Type (FTDP), Pick's disease, Niemann-Pick's Disease, Huntington's Disease, Huntington's chorea, tardive dyskinesia, hyperkinesia, progressive supranuclear palsy, progressive supranuclear paresis, restless leg syndrome, Creutzfeld-Jakob disease, multiple sclerosis, amyotrophic lateral sclerosis (ALS), motor neuron diseases (MND), multiple system atrophy (MSA), corticobasal degeneration, Guillain-Barré Syndrome (GBS), and chronic inflammatory demyelinating polyneuropathy (CIDP), epilepsy, autosomal dominant nocturnal frontal lobe epilepsy, mania, anxiety, depression, premenstrual dysphoria, panic disorders, bulimia, anorexia, narcolepsy, excessive daytime sleepiness, bipolar disorders, generalized anxiety disorder, obsessive compulsive disorder, rage outbursts, oppositional defiant disorder, Tourette's syndrome, autism, drug and alcohol addiction, tobacco addiction, obesity, cachexia, psoriasis, lupus, acute cholangitis, aphthous stomatitis, ulcers, asthma, ulcerative colitis, inflammatory bowel disease, Crohn's disease, spastic dystonia, diarrhea, constipation, pouchitis, viral pneumonitis, arthritis, including, rheumatoid arthritis and osteoarthritis, endotoxaemia, sepsis, atherosclerosis, idiopathic pulmonary fibrosis, acute pain, chronic pain, neuropathies, urinary incontinence, diabetes and neoplasias.

Cognitive impairments or dysfunctions may be associated with psychiatric disorders or conditions, such as schizophrenia and other psychotic disorders (including but not limited to psychotic disorder, schizophreniform disorder, schizoaffective disorder, delusional disorder, brief psychotic disorder, shared psychotic disorder, and psychotic disorders due to a general medical conditions), dementias and other cognitive disorders (including but not limited to mild cognitive impairment, pre-senile dementia, Alzheimer's disease, senile dementia, dementia of the Alzheimer's type, age-related memory impairment, Lewy body dementia, vascular dementia, AIDS dementia complex, dyslexia, Parkinsonism including Parkinson's disease, cognitive impairment and dementia of Parkinson's Disease, cognitive impairment of multiple sclerosis, cognitive impairment caused by traumatic brain injury, dementias due to other general medical conditions), anxiety disorders (including but not limited to panic disorder without agoraphobia, panic disorder with agoraphobia, agoraphobia without history of panic disorder, specific phobia, social phobia, obsessive-compulsive disorder, post-traumatic stress disorder, acute stress disorder, generalized anxiety disorder and generalized anxiety disorder due to a general medical condition), mood disorders (including but not limited to major depressive disorder, dysthymic disorder, bipolar depression, bipolar mania, bipolar I disorder, depression associated with manic, depressive or mixed episodes, bipolar II disorder, cyclothymic disorder, and mood disorders due to general medical conditions), sleep disorders (including but not limited to dyssomnia disorders, primary insomnia, primary hypersomnia, narcolepsy, parasomnia disorders, nightmare disorder, sleep terror disorder and sleepwalking disorder), mental retardation, learning disorders, motor skills disorders, communication disorders, pervasive developmental disorders, attention-deficit and disruptive behavior disorders, attention deficit disorder, attention deficit hyperactivity disorder, feeding and eating disorders of infancy, childhood or adults, tic disorders, elimination disorders, substance-related disorders (including but not limited to substance dependence, substance abuse, substance intoxication, substance withdrawal, alcohol-related disorders, amphetamine or amphetamine-like-related disorders, caffeine-related disorders, cannabis-related disorders, cocaine-related disorders, hallucinogen-related disorders, inhalant-related disorders, nicotine-related disorders, opioid-related disorders, phencyclidine or phencyclidine-like-related disorders, and sedative-, hypnotic- or anxiolytic-related disorders), personality disorders (including but not limited to obsessive-compulsive personality disorder and impulse-control disorders).

The above conditions and disorders are defined for example in the American Psychiatric Association: Diagnostic and Statistical Manual of Mental Disorders, Fourth Edition, Text Revision, Washington, D.C., American Psychiatric Association, 2000. This Manual may also be referred to for greater detail on the symptoms and diagnostic features associated with substance use, abuse, and dependence, and is herein incorporated by reference with regard to such.

Preferably, the treatment or prevention of diseases, disorders and conditions occurs without appreciable adverse side effects, including, for example, significant increases in blood pressure and heart rate, significant negative effects upon the gastro-intestinal tract, and significant effects upon skeletal muscle.

The compounds of the present invention, when employed in effective amounts, can modulate the activity of the α4β2 NNRs without appreciable interaction with the nicotinic subtypes that characterize the human ganglia, as demonstrated by their lack of the ability of to elicit nicotinic function in adrenal chromaffin tissue, or skeletal muscle, as demonstrated by their lack of ability to elicit nicotinic function in cell preparations expressing muscle-type nicotinic receptors. Thus, these compounds are capable of treating or preventing diseases, disorders and conditions without eliciting significant side effects associated activity at ganglionic and neuromuscular sites. Thus, administration of the compounds is believed to provide a therapeutic window in which treatment of certain diseases, disorders and conditions is provided, and certain side effects are avoided. That is, an effective dose of the compound is sufficient to provide the desired effects upon the disease, disorder or condition, but is insufficient, namely is not at a high enough level, to provide undesirable side effects.

Thus, the present invention provides the use of a compound of the present invention, or a pharmaceutically acceptable salt thereof, for use in therapy, such such as any one of the therapies described above.

In yet another aspect the present invention provides the use of a compound of the present invention, or a pharmaceutically acceptable salt thereof, in the manufacture of a medicament for the treatment of a CNS disorder, such as a disorder, disease or condition described hereinabove.

In a further aspect the invention provides the use of a compound of the present invention, or a pharmaceutically acceptable salt thereof, in the manufacture of a medicament for the treatment mild to moderate dementia of the Alzheimer's type, attention deficit disorder, mild cognitive impairment, age-associated memory impairment and cognitive dysfunction in schizophrenia.

Diagnostic Uses

The compounds can be used in diagnostic compositions, such as probes, particularly when they are modified to include appropriate labels. The probes can be used, for example, to determine the relative number and/or function of specific receptors, particularly the α4β2 receptor subtype. For this purpose the compounds of the present invention most preferably are labeled with a radioactive isotopic moiety such as $^{11}C$, $^{18}F$, $^{76}Br$, $^{123}I$ or $^{125}I$.

The administered compounds can be detected using known detection methods appropriate for the label used. Examples of detection methods include position emission topography (PET) and single-photon emission computed tomography (SPECT). The radiolabels described above are useful in PET (e.g., $^{11}C$, $^{18}F$ or $^{76}Br$) and SPECT (e.g., $^{123}I$) imaging, with half-lives of about 20.4 minutes for $^{11}C$, about 109 minutes for $^{18}F$, about 13 hours for $^{123}I$, and about 16 hours for $^{76}Br$. A high specific activity is desired to visualize the selected receptor subtypes at non-saturating concentrations. The administered doses typically are below the toxic range and provide high contrast images. The compounds are expected to be capable of administration in non-toxic levels. Determination of dose is carried out in a manner known to one skilled in the art of radiolabel imaging. See, for example, U.S. Pat. No. 5,969,144 to London et al.

The compounds can be administered using known techniques. See, for example, U.S. Pat. No. 5,969,144 to London et al, herein incorporated by reference with regard to such techniques. The compounds can be administered in formulation compositions that incorporate other ingredients, such as those types of ingredients that are useful in formulating a diagnostic composition. Compounds useful in accordance with carrying out the present invention most preferably are employed in forms of high purity. See, U.S. Pat. No. 5,853,696 to Elmalch et al.

After the compounds are administered to a subject (e.g., a human subject), the presence of that compound within the subject can be imaged and quantified by appropriate techniques in order to indicate the presence, quantity, and functionality of selected nicotinic cholinergic receptor subtypes. In addition to humans, the compounds can also be administered to animals, such as mice, rats, dogs, and monkeys. SPECT and PET imaging can be carried out using any appropriate technique and apparatus. See Villemagne et al., In: Americ et al. (Eds.) *Neuronal Nicotinic Receptors: Pharmacology and Therapeutic Opportunities*, 235-250 (1998) and U.S. Pat. No. 5,853,696 to Elmalch et al. for a disclosure of representative imaging techniques; each herein incorporated by reference with regard to such teaching.

The radiolabeled compounds bind with high affinity to selective nAChR subtypes (e.g., α4β2) and preferably exhibit negligible non-specific binding to other nicotinic cholinergic receptor subtypes (e.g., those receptor subtypes associated with muscle and ganglia). As such, the compounds can be used as agents for noninvasive imaging of nicotinic cholinergic receptor subtypes within the body of a subject, particularly within the brain for diagnosis associated with a variety of CNS diseases and disorders.

In one aspect, the diagnostic compositions can be used in a method to diagnose disease in a subject, such as a human patient. The method involves administering to that patient a detectably labeled compound as described herein, and detecting the binding of that compound to selected nicotinic receptor subtypes (e.g., α4β2 receptor subtype). Those skilled in the art of using diagnostic tools, such as PET and SPECT, can use the radiolabeled compounds described herein to diagnose a wide variety of conditions and disorders, including conditions and disorders associated with dysfunction of the central and autonomic nervous systems. Such disorders include a wide variety of CNS diseases and disorders, including Alzheimer's disease, Parkinson's disease, and schizophrenia. These and other representative diseases and disorders that can be evaluated include those that are set forth herein as well as in U.S. Pat. No. 5,952,339 to Bencherif et al., herein incorporated by reference in entirety.

In another aspect, the diagnostic compositions can be used in a method to monitor selective nicotinic receptor subtypes of a subject, such as a human patient. The method involves administering a detectably labeled compound as described herein to that patient and detecting the binding of that compound to selected nicotinic receptor subtypes (e.g., the α4β2 receptor subtype).

Pharmaceutical Compositions

The pharmaceutical compositions of the present invention incorporate a compound of the present invention which, when employed in effective amounts, interacts with relevant nicotinic receptor sites of a subject, and acts as a therapeutic agent to treat and prevent a wide variety of conditions and disorders. The pharmaceutical compositions provide therapeutic benefit to individuals suffering from affected disorders or exhibiting clinical manifestations of affected disorders, in that the compounds within those compositions, when employed in effective amounts, can: (i) exhibit nicotinic pharmacology and affect relevant nicotinic receptors sites, for example by acting as a pharmacological agonist to activate a nicotinic receptor; or (ii) elicit neurotransmitter secretion, and hence prevent and suppress the symptoms associated with those diseases.

The compounds of the present invention have the potential to (i) increase the number of nicotinic cholinergic receptors of the brain of a subject in need thereof; (ii) exhibit neuroprotective effects; and (iii) when employed in effective amounts, to not cause appreciable adverse side effects, for example, significant increases in blood pressure and heart rate, significant negative effects upon the gastro-intestinal tract, or significant effects upon skeletal muscle.

The present invention further provides pharmaceutical compositions that include effective amounts of compounds of the formulae of the present invention and salts and solvates, thereof, and one or more pharmaceutically acceptable carriers, diluents, or excipients. The compounds of the formulae of the present invention, including salts and solvates, thereof, are as herein described. The carrier(s), diluent(s), or excipient(s) must be acceptable, in the sense of being compatible with the other ingredients of the formulation and not deleterious to the recipient of the pharmaceutical composition.

In accordance with another aspect of the invention there is also provided a process for the preparation of a pharmaceutical formulation including admixing a compound of the formulae of the present invention, including a salt, solvate, or prodrug thereof, with one or more pharmaceutically acceptable carriers, diluents or excipients.

The manner in which the compounds are administered can vary. The compositions are preferably administered orally (e.g., in liquid form within a solvent such as an aqueous or non-aqueous liquid, or within a solid carrier). Preferred compositions for oral administration include pills, tablets, capsules, caplets, syrups, and solutions, including hard gelatin capsules and time-release capsules. Compositions may be formulated in unit dose form, or in multiple or subunit doses. Preferred compositions are in liquid or semisolid form.

Compositions including a liquid pharmaceutically inert carrier such as water or other pharmaceutically compatible liquids or semisolids may be used. The use of such liquids and semisolids is well known to those of skill in the art.

The compositions can also be administered via injection, i.e., intravenously, intramuscularly, subcutaneously, intraperitoneally, intraarterially, intrathecally, and intracerebroventricularly. Intravenous administration is a preferred method of injection. Suitable carriers for injection are well known to those of skill in the art, and include 5% dextrose solutions, saline, and phosphate buffered saline. The compounds can also be administered as an infusion or injection (e.g., as a suspension or as an emulsion in a pharmaceutically acceptable liquid or mixture of liquids).

The formulations may also be administered using other means, for example, rectal administration. Formulations useful for rectal administration, such as suppositories, are well known to those of skill in the art. The compounds can also be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); transdermally (e.g., using a transdermal patch, using technology that is commercially available from Novartis and Alza Corporation, or by powder injection); or by buccal or intranasal absorption. Although it is possible to administer the compounds in the form of a bulk active chemical, it is preferred to present each compound in the form of a pharmaceutical composition or formulation for efficient and effective administration.

Exemplary methods for administering such compounds will be apparent to the skilled artisan. The usefulness of these formulations may depend on the particular composition used and the particular subject receiving the treatment. For example, the compositions can be administered in the form of a tablet, a hard gelatin capsule or as a time release capsule. These formulations may contain a liquid carrier that may be oily, aqueous, emulsified or contain certain solvents suitable to the mode of administration.

The administration of the pharmaceutical compositions described herein can be intermittent, or at a gradual, continuous, constant or controlled rate to a warm-blooded animal, (e.g., a mammal such as a mouse, rat, cat, rabbit, dog, pig, cow, or monkey); but advantageously is preferably administered to a human being. In addition, the time of day and the number of times per day that the pharmaceutical composition is administered can vary.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder. Thus, when treating a CNS disorder, an effective amount of compound is an amount sufficient to pass across the blood-brain barrier of the subject, to bind to relevant receptor sites in the brain of the subject, and to modulate the activity of relevant nicotinic receptor subtypes (e.g., modulate neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the reoccurrence of the symptoms of the disorder.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to modulate disease-relevant receptors to affect neurotransmitter (e.g., dopamine) release but the amount should be insufficient to induce effects on skeletal muscles and ganglia to any significant degree. The effective dose of compounds will of course differ from patient to patient but in general includes amounts starting where CNS effects or other desired therapeutic effects occur, but below the amount where muscular and ganglionic effects are observed.

Typically, to be administered in an effective dose, compounds require administering in an amount of less than 5 mg/kg of patient weight. Often, the compounds may be administered in an amount from less than about 1 mg/kg patient weight to less than about 100 µg/kg of patient weight, and occasionally between about 10 µg/kg to less than 100 µg/kg of patient weight. The foregoing effective doses typically represent that amount administered as a single dose, or as one or more doses administered over a 24 hours period. For human patients, the effective dose of the compounds may require administering the compound in an amount of at least about 1, but not more than about 1000, and often not more than about 500 mg/24 hr/patient.

Compositions useful as diagnostics can be employed, as set forth in U.S. Pat. No. 5,853,696 to Elmalch et al. and U.S. Pat. No. 5,969,144 to London et al., the contents of which are hereby incorporated by reference. The compounds also can be administered in formulation compositions that incorporate other ingredients, such as those types of ingredients that are useful in formulating a diagnostic composition.

The present invention also encompasses combination therapy for treating or preventing a disorder mediated by a NNR or nAChR in a subject. The combination therapy comprises administering to the subject a therapeutically or prophylactically effective amount of a compound of the present invention and one or more other therapy including chemotherapy, radiation therapy, gene therapy, or immunotherapy.

In an embodiment of the present invention, the compound of the present invention may be administered in combination with other therapeutic compounds. In particular, a compound of this invention can be advantageously used in combination with other NNR ligands (such as varenicline), antioxidants (such as free radical scavenging agents), antibacterial agents (such as penicillin antibiotics), antiviral agents (such as nucleoside analogs, like zidovudine and acyclovir), anticoagulants (such as warfarin), anti-inflammatory agents (such as NSAIDs), anti-pyretics, analgesics, anesthetics (such as used in surgery), acetylcholinesterase inhibitors (such as donepezil and galantamine), antipsychotics (such as haloperidol, clozapine olanzapine and quetiapine), immuno-suppressants (such as cyclosporin and methotrexate), neuroprotective agents, steroids (such as steroid hormones), corticosteroids (such as dexamethasone, predisone and hydrocortisone), vitamins, minerals, nutraceuticals, anti-depressants (such as imipramine, fluoxetine, paroxetine, escitalopram, sertraline, venlafaxine and duloxetine), anxiolytics (such as alprazolam and buspirone), anticonvulsants (such as phenytoin and gabapentin), vasodilators (such as prazosin and sildenafil), mood stabilizers (such as valproate and aripiprazole), anti-cancer drugs (such as anti-proliferatives), anti-hypertensive agents (such as atenolol, clonidine, amlopidine, verapamil and olmesartan), laxatives, stool softeners, diuretics (such as furosemide), anti-spasmotics (such as dicyclomine), anti-dyskinetic agents, and anti-ulcer medications (such as esomeprazole).

The compounds of the present invention may be employed alone or in combination with other therapeutic agents, including other compounds of the present invention. Such a combination of pharmaceutically active agents may be administered together or separately and, when administered separately, administration may occur simultaneously or sequentially, in any order. The amounts of the compounds or agents and the relative timings of administration will be selected in order to achieve the desired therapeutic effect. The administration in combination of a compound of the formulae of the present invention including salts or solvates thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time. The compounds of the present invention may be used in the treatment of a variety of disorders and conditions and, as such, the compounds of the present invention may be used in combination with a variety of other suitable therapeutic agents useful in the treatment and/or prophylaxis of those disorders or conditions.

The following examples are provided to illustrate the present invention, and should not be construed as limiting thereof. In these examples, all parts and percentages are by weight, unless otherwise noted.

LIST OF ABBREVIATIONS

The following definitions for abbreviations used herein are meant to clarify, but not limit, the terms defined. If a particular abbreviation used herein is not specifically defined, the abbreviation term should not be considered indefinite. Rather, abbreviations are used within their accepted meanings in the art.
THF (tetrahydrofuran)
DIPEA (diisopropylethylamine)
DMF (dimethylformamide)
HBTU (O-(benzotriazol-1-yl)-N,N,N',N'-tetramethyluronium hexafluorophosphate)
DMAP (4-N,N-dimethylaminopyridine)
CMA 90 (chloroform:methanol:aqueous ammonium hydroxide (90:9:1))
DCC (N,N'-dicyclohexylcarbodiimide)
PS-DCC (polystyrene bound N,N'-dicyclohexylcarbodiimide)
HOBt (1-hydroxybenzotriazole)
TFA (trifluoroacetic acid)
HPLC (high performance liquid chromatography)
MLA (methyllycaconitine)
NOR (novel object recognition)
ND (not determined)
[$^3$H] tritium, labeled with radioactive hydrogen
[$^3$H]DA dopamine radiolabeled with tritium
[$^3$H]MLA methyllycaconitine radiolabeled with tritium
[$^3$H]QNB 3-quinuclidinyl benzilate radiolabeled with tritium
° C. degrees celsius
$^{86}$Rb$^+$ radioactive rubidium
AIDS Acquired Immune Deficiency Syndrome
$CaCl_2$ calcium chloride
Ci Curie
CNS central nervous system
$CO_2$ carbon dioxide
DA dopamine
$EC_{50}$ drug concentration that provokes a half-maximal response
EDTA ethylenediaminetetraacetic acid
$E_{max}$ maximal effect
g grams
g unit of force to which a body is subjected when undergoing acceleration
GF/B glass fiber filter, pore size B
h hours
HEPES 4-(2-hydroxyethyl)-1-piperazineethanesulfonic acid
HIV Human Immunodeficiency Virus
HTS high throughput screening
$IC_{50}$ concentration that inhibits activity by 50 percent
KCl potassium chloride
$KH_2PO_4$ potassium phosphate, monobasic equilibrium dissociation constant for competitor inhibited radioligand
$K_i$ binding
M molar
mg milligram
μg microgram
$MgCl_2$ magnesium chloride
Min minutes
mL milliliter
μl microliter
MLA methyllycaconitine
mM millimolar
μM micromolar
mmol millimol
$Na_2HPO_4$ sodium phosphate, dibasic
nAChR nicotinic acetylcholine receptor
nAChRs nicotinic acetylcholine receptors
NaCl sodium chloride
nM nanomolar
NNR neuronal nicotinic receptor
NNRs neuronal nicotinic receptors
NOR novel object recognition
NSAIDs nonsteroidal anti-inflammatory drugs
PBS phosphate buffered saline
PET positron emission tomography
pH negative logarithm of the effective hydrogen ion concentration
PMSF phenylmethylsulphonyl fluoride
QNB 3-quinuclidinyl benzilate
SPECT single-photon emission computed tomography

BIOLOGICAL ASSAYS

Example 1

Radioligand Binding at CNS nAChRs

α4β2 nAChR Subtype

Rats (female, Sprague-Dawley), weighing 150-250 g, were maintained on a 12 h light/dark cycle and were allowed free access to water and food supplied by PMI Nutrition International, Inc. Animals were anesthetized with 70% $CO_2$, then decapitated. Brains were removed and placed on an ice-cold platform. The cerebral cortex was removed and placed in 20 volumes (weight:volume) of ice-cold preparative buffer (137 mM NaCl, 10.7 mM KCl, 5.8 mM $KH_2PO_4$, 8 mM $Na_2HPO_4$, 20 mM HEPES (free acid), 5 mM iodoacetamide, 1.6 mM EDTA, pH 7.4); PMSF, dissolved in methanol to a final concentration of 100 μM, was added and the suspension was homogenized by Polytron. The homogenate was centrifuged at 18,000×g for 20 min at 4° C. and the resulting pellet was re-suspended in 20 volumes of ice-cold water. After 60 min incubation on ice, a new pellet was collected by centrifugation at 18,000×g for 20 min at 4° C. The final pellet was re-suspended in 10 volumes of buffer and stored at −20° C. On the day of the assay, tissue was thawed, centrifuged at 18,000×g for 20 min, and then re-suspended in ice-cold PBS (Dulbecco's Phosphate Buffered Saline, 138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4) to a final concentration of approximately 4 mg protein/mL. Protein was determined by the method of Lowry et al., *J. Biol. Chem.* 193: 265 (1951), using bovine serum albumin as the standard.

The binding of [$^3$H]nicotine was measured using a modification of the methods of Romano at al., *Science* 210: 647 (1980) and Marks et al., *Mol. Pharmacol.* 30: 427 (1986). The [$^3$H]nicotine (Specific Activity=81.5 Ci/mmol) was obtained from NEN Research Products. The binding of [$^3$H]nicotine was measured using a 3 h incubation at 4° C. Incubations were conducted in 48-well micro-titre plates and contained about 400 μg of protein per well in a final incubation volume of 300 μL. The incubation buffer was PBS and the final concentration of [$^3$H]nicotine was 5 nM. The binding reaction was terminated by filtration of the protein containing bound ligand onto glass fiber filters (GF/B, Brandel) using a Brandel Tissue Harvester at 4° C. Filters were soaked in de-ionized water containing 0.33% polyethyleneimine to reduce non-specific binding. Each filter was washed with ice-cold buffer (3×1 mL). Non-specific binding was determined by inclusion of 10 μM non-radioactive L-nicotine (Acros Organics) in selected wells.

The inhibition of [$^3$H]nicotine binding by test compounds was determined by including seven different concentrations of the test compound in selected wells. Each concentration was replicated in triplicate. $IC_{50}$ values were estimated as the concentration of compound that inhibited 50 percent of specific [$^3$H]nicotine binding. Inhibition constants (Ki values), reported in nM, were calculated from the $IC_{50}$ values using the method of Cheng et al., *Biochem. Pharmacol.* 22: 3099 (1973).

α7 nAChR Subtype

Rats (female, Sprague-Dawley), weighing 150-250 g, were maintained on a 12 h light/dark cycle and were allowed free access to water and food supplied by PMI Nutrition International, Inc. Animals were anesthetized with 70% $CO_2$, then decapitated. Brains were removed and placed on an ice-cold platform. The hippocampus was removed and placed in 10 volumes (weight:volume) of ice-cold preparative buffer (137 mM NaCl, 10.7 mM KCl, 5.8 mM $KH_2PO_4$, 8 mM $Na_2HPO_4$, 20 mM HEPES (free acid), 5 mM iodoacetamide, 1.6 mM EDTA, pH 7.4); PMSF, dissolved in methanol to a final concentration of 100 μM, was added and the tissue suspension was homogenized by Polytron. The homogenate was centrifuged at 18,000×g for 20 min at 4° C. and the resulting pellet was re-suspended in 10 volumes of ice-cold water. After 60 min incubation on ice, a new pellet was collected by centrifugation at 18,000×g for 20 min at 4° C. The final pellet was re-suspended in 10 volumes of buffer and stored at −20° C. On the day of the assay, tissue was thawed, centrifuged at 18,000×g for 20 min, and then re-suspended in ice-cold PBS (Dulbecco's Phosphate Buffered Saline, 138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4) to a final concentration of approximately 2 mg protein/m L. Protein was determined by the method of Lowry et al., *J. Biol. Chem.* 193: 265 (1951), using bovine serum albumin as the standard.

The binding of [$^3$H]MLA was measured using a modification of the methods of Davies et al., *Neuropharmacol.* 38: 679 (1999). [$^3$H]MLA (Specific Activity=25-35 Ci/mmol) was obtained from Tocris. The binding of [$^3$H]MLA was determined using a 2 h incubation at 21° C. Incubations were conducted in 48-well micro-titre plates and contained about 200 μg of protein per well in a final incubation volume of 300 μL. The incubation buffer was PBS and the final concentration of [$^3$H]MLA was 5 nM. The binding reaction was terminated by filtration of the protein containing bound ligand onto glass fiber filters (GF/B, Brandel) using a Brandel Tissue Harvester at room temperature. Filters were soaked in de-ionized water containing 0.33% polyethyleneimine to reduce non-specific binding. Each filter was washed with PBS (3×1 mL) at room temperature. Non-specific binding was determined by inclusion of 50 μM non-radioactive MLA in selected wells.

The inhibition of [$^3$H]MLA binding by test compounds was determined by including seven different concentrations of the test compound in selected wells. Each concentration was replicated in triplicate. $IC_{50}$ values were estimated as the concentration of compound that inhibited 50 percent of specific [$^3$H]MLA binding. Inhibition constants (Ki values), reported in nM, were calculated from the $IC_{50}$ values using the method of Cheng et al., *Biochem. Pharmacol.* 22: 3099-3108 (1973).

Example 2

Determination of Dopamine Release

Dopamine release was measured using striatal synaptosomes obtained from rat brain, according to the procedures set forth by Rapier et al., *J. Neurochem.* 54: 937 (1990). Rats (female, Sprague-Dawley), weighing 150-250 g, were maintained on a 12 h light/dark cycle and were allowed free access to water and food supplied by PMI Nutrition International, Inc. Animals were anesthetized with 70% $CO_2$, then decapitated. The brains were quickly removed and the striata dissected. Striatal tissue from each of 2 rats was pooled and homogenized in ice-cold 0.32 M sucrose (5 mL) containing 5 mM HEPES, pH 7.4, using a glass/glass homogenizer. The tissue was then centrifuged at 1,000×g for 10 min. The pellet was discarded and the supernatant was centrifuged at 12,000×g for 20 min. The resulting pellet was re-suspended in perfusion buffer containing monoamine oxidase inhibitors (128 mM NaCl, 1.2 mM $KH_2PO_4$, 2.4 mM KCl, 3.2 mM $CaCl_2$, 1.2 mM $MgSO_4$, 25 mM HEPES, 1 mM ascorbic acid, 0.02 mM pargyline Hydrochloric acid and 10 mM glucose, pH 7.4) and centrifuged for 15 min at 25,000×g. The final pellet was resuspended in perfusion buffer (1.4 mL) for immediate use.

The synaptosomal suspension was incubated for 10 min at 37° C. to restore metabolic activity. [$^3$H]Dopamine ([$^3$H]DA, specific activity=28.0 Ci/mmol, NEN Research Products) was added at a final concentration of 0.1 µM and the suspension was incubated at 37° C. for another 10 min. Aliquots of tissue (50 µL) and perfusion buffer (100 µL) were loaded into the suprafusion chambers of a Brandel Suprafusion System (series 2500, Gaithersburg, Md.). Perfusion buffer (room temperature) was pumped into the chambers at a rate of 3 mL/min for a wash period of 8 min. Test compound (10 µM) or nicotine (10 µM) was then applied in the perfusion stream for 40 sec. Fractions (12 sec each) were continuously collected from each chamber throughout the experiment to capture basal release and agonist-induced peak release and to re-establish the baseline after the agonist application. The perfusate was collected directly into scintillation vials, to which scintillation fluid was added. [$^3$H]DA released was quantified by scintillation counting. For each chamber, the integrated area of the peak was normalized to its baseline.

Release was expressed as a percentage of release obtained with an equal concentration of L-nicotine. Within each assay, each test compound was replicated using 2-3 chambers; replicates were averaged. When appropriate, dose-response curves of test compound were determined. The maximal activation for individual compounds (Emax) was determined as a percentage of the maximal activation induced by L-nicotine. The compound concentration resulting in half maximal activation (EC$_{50}$) of specific ion flux was also defined.

Example 3

Selectivity vs. Peripheral nAChRs

Interaction at the Human Muscle nAChR Subtype

Activation of muscle-type nAChRs was established on the human clonal line TE671/RD, which is derived from an embryonal rhabdomyosarcoma (Stratton et al., Carcinogen 10: 899 (1989)). These cells express receptors that have pharmacological (Lukas, *J. Pharmacol. Exp. Ther.* 251:175 (1989)), electrophysiological (Oswald et al., *Neurosci. Lett.* 96: 207 (1989)), and molecular biological profiles (Luther et al., *J. Neurosci.* 9: 1082 (1989)) similar to the muscle-type nAChR.

TE671/RD cells were maintained in proliferative growth phase according to routine protocols (Bencherif et al., *Mol. Cell. Neurosci.* 2: 52 (1991) and Bencherif et al., *J. Pharmacol. Exp. Ther.* 257: 946 (1991)). Cells were cultured in Dulbecco's modified Eagle's medium (Gibco/BRL) with 10% horse serum (Gibco/BRL), 5% fetal bovine serum (HyClone, Logan, Utah), 1 mM sodium pyruvate, 4 mM L-Glutamine, and 50,000 units penicillin-streptomycin (Irvine Scientific). When cells were 80% confluent, they were plated to 12 well polystyrene plates (Costar). Experiments were conducted when the cells reached 100% confluency.

Nicotinic acetylcholine receptor (nAChR) function was assayed using $^{86}$Rb$^+$ efflux according to the method described by Lukas et al., *Anal. Biochem.* 175: 212 (1988). On the day of the experiment, growth media was gently removed from the well and growth media containing $^{86}$Rubidium chloride (10$^6$ µCi/mL) was added to each well. Cells were incubated at 37° C. for a minimum of 3 h. After the loading period, excess $^{86}$Rb$^+$ was removed and the cells were washed twice with label-free Dulbecco's phosphate buffered saline (138 mM NaCl, 2.67 mM KCl, 1.47 mM KH$_2$PO$_4$, 8.1 mM Na$_2$HPO$_4$, 0.9 mM CaCl$_2$, 0.5 mM MgCl$_2$, Invitrogen/Gibco, pH. 7.4), taking care not to disturb the cells. Next, cells were exposed to either 100 µM of test compound, 100 µM of L-nicotine (Acros Organics) or buffer alone for 4 min. Following the exposure period, the supernatant containing the released $^{86}$Rb$^+$ was removed and transferred to scintillation vials. Scintillation fluid was added and released radioactivity was measured by liquid scintillation counting.

Within each assay, each point had 2 replicates, which were averaged. The amount of $^{86}$Rb$^+$ release was compared to both a positive control (100 µM L-nicotine) and a negative control (buffer alone) to determine the percent release relative to that of L-nicotine.

When appropriate, dose-response curves of test compound were determined. The maximal activation for individual compounds (Emax) was determined as a percentage of the maximal activation induced by L-nicotine. The compound concentration resulting in half maximal activation (EC$_{50}$) of specific ion flux was also determined.

Interaction at the Rat Ganglionic nAChR Subtype

Activation of rat ganglion nAChRs was established on the pheochromocytoma clonal line PC12, which is a continuous clonal cell line of neural crest origin, derived from a tumor of the rat adrenal medulla. These cells express ganglion-like nAChR s (see Whiting et al., *Nature* 327: 515 (1987); Lukas, *J. Pharmacol. Exp. Ther.* 251: 175 (1989); Whiting et al., *Mol. Brain Res.* 10: 61 (1990)).

Rat PC12 cells were maintained in proliferative growth phase according to routine protocols (Bencherif et al., *Mol. Cell. Neurosci.* 2: 52 (1991) and Bencherif et al., *J. Pharmacol. Exp. Ther.* 257: 946 (1991)). Cells were cultured in Dulbecco's modified Eagle's medium (Gibco/BRL) with 10% horse serum (Gibco/BRL), 5% fetal bovine serum (HyClone, Logan, Utah), 1 mM sodium pyruvate, 4 mM L-Glutamine, and 50,000 units penicillin-streptomycin (Irvine Scientific). When cells were 80% confluent, they were plated to 12 well Nunc plates (Nunclon) and coated with 0.03% poly-L-lysine (Sigma, dissolved in 100 mM boric acid). Experiments were conducted when the cells reached 80% confluency.

Nicotinic acetylcholine receptor (nAChR) function was assayed using $^{86}$Rb$^+$ efflux according to a method described by Lukas et al., *Anal. Biochem.* 175: 212 (1988). On the day of the experiment, growth media was gently removed from the well and growth media containing $^{86}$Rubidium chloride (10$^6$ µCi/mL) was added to each well. Cells were incubated at 37° C. for a minimum of 3 h. After the loading period, excess $^{86}$Rb$^+$ was removed and the cells were washed twice with label-free Dulbecco's phosphate buffered saline (138 mM NaCl, 2.67 mM KCl, 1.47 mM KH$_2$PO$_4$, 8.1 mM Na$_2$HPO$_4$, 0.9 mM CaCl$_2$, 0.5 mM MgCl$_2$, Invitrogen/Gibco, pH. 7.4), taking care not to disturb the cells. Next, cells were exposed to either 100 µM of test compound, 100 µM of nicotine or buffer alone for 4 min. Following the exposure period, the supernatant containing the released $^{86}$Rb$^+$ was removed and transferred to scintillation vials. Scintillation fluid was added and released radioactivity was measured by liquid scintillation counting Within each assay, each point had 2 replicates, which were averaged. The amount of $^{86}$Rb$^+$ release was compared to both a positive control (100 µM nicotine) and a negative control (buffer alone) to determine the percent release relative to that of L-nicotine.

When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also determined.

Interaction at the Human Ganglionic nAChR Subtype

The cell line SH-SY5Y is a continuous line derived by sequential subcloning of the parental cell line, SK-N-SH, which was originally obtained from a human peripheral neuroblastoma. SH-SY5Y cells express a ganglion-like nAChR (Lukas et al., *Mol. Cell. Neurosci.* 4: 1 (1993)).

Human SH-SY5Y cells were maintained in proliferative growth phase according to routine protocols (Bencherif et al., *Mol. Cell. Neurosci.* 2: 52 (1991) and Bencherif et al., *J. Pharmacol. Exp. Ther.* 257: 946 (1991)). Cells were cultured in Dulbecco's modified Eagle's medium (Gibco/BRL) with 10% horse serum (Gibco/BRL), 5% fetal bovine serum (HyClone, Logan, Utah), 1 mM sodium pyruvate, 4 mM L-Glutamine, and 50,000 units penicillin-streptomycin (Irvine Scientific). When cells were 80% confluent, they were plated to 12 well polystyrene plates (Costar). Experiments were conducted when the cells reached 100% confluency.

Nicotinic acetylcholine receptor (nAChR) function was assayed using $^{86}Rb^+$ efflux according to a method described by Lukas et al., *Anal. Biochem.* 175: 212 (1988). On the day of the experiment, growth media was gently removed from the well and growth media containing $^{86}$Rubidium chloride ($10^6$ µCi/mL) was added to each well. Cells were incubated at 37° C. for a minimum of 3 h. After the loading period, excess $^{86}Rb^+$ was removed and the cells were washed twice with label-free Dulbecco's phosphate buffered saline (138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4), taking care not to disturb the cells. Next, cells were exposed to either 100 µM of test compound, 100 µM of nicotine, or buffer alone for 4 min. Following the exposure period, the supernatant containing the released $^{86}Rb^+$ was removed and transferred to scintillation vials. Scintillation fluid was added and released radioactivity was measured by liquid scintillation counting Within each assay, each point had 2 replicates, which were averaged. The amount of $^{86}Rb^+$ release was compared to both a positive control (100 µM nicotine) and a negative control (buffer alone) to determine the percent release relative to that of L-nicotine.

When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also defined.

Example 4

Determination of Binding at Non-Nicotinic Receptors

Muscarinic M3 Subtype

The human clonal line TE671/RD, derived from an embryonal rhabdomyosarcoma (Stratton et al., *Carcinogen* 10: 899 (1989)), was used to define binding to the muscarinic M3 receptor subtype. As evidenced through pharmacological (Bencherif et al., *J. Pharmacol. Exp. Ther.* 257: 946 (1991) and Lukas, *J. Pharmacol. Exp. Ther.* 251: 175 (1989)), electrophysiological (Oswald et al., *Neurosci. Lett.* 96: 207 (1989)), and molecular biological studies (Luther et al., *J. Neurosci.* 9: 1082 (1989)) these cells express muscle-like nicotinic receptors. TE671/RD cells were maintained in proliferative growth phase according to routine protocols (Bencherif et al., *Mol. Cell. Neurosci.* 2: 52 (1991) and Bencherif et al., *J. Pharmacol. Exp. Ther.* 257: 946 (1991)). They were grown to confluency on 20-150 mm tissue culture treated plates. The media was then removed and cells scraped using 80 mL of PBS (Dulbecco's Phosphate Buffered Saline, 138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4) and then centrifuged at 1000 rpm for 10 min. The supernatant was then suctioned off and the pellet(s) stored at −20° C. until use.

On the day of the assay, the pellets were thawed, re-suspended with PBS and centrifuged at 18,000×g for 20 min, then re-suspended in PBS to a final concentration of approximately 4 mg protein/mL and homogenized by Polytron. Protein was determined by the method of Lowry et al., *J. Biol. Chem.* 193: 265 (1951), using bovine serum albumin as the standard.

The binding of [$^3$H]QNB was measured using a modification of the methods of Bencherif et al., *J. Pharmacol. Exp. Ther.* 257: 946 (1991). [$^3$H]QNB (Specific Activity=30-60 Ci/mmol) was obtained from NEN Research Products. The binding of [$^3$H]QNB was measured using a 3 h incubation at 4° C. Incubations were conducted in 48-well micro-titre plates and contained about 400 µg of protein per well in a final incubation volume of 300 µL. The incubation buffer was PBS and the final concentration of [$^3$H]QNB was 1 nM. The binding reaction was terminated by filtration of the protein containing bound ligand onto glass fiber filters (GF/B, Brandel) using a Brandel Tissue Harvester at 4° C. Filters were presoaked in de-ionized water containing 0.33% polyethyleneimine to reduce non-specific binding. Each filter was washed with ice-cold buffer (3×1 mL). Non-specific binding was determined by inclusion of 10 µM non-radioactive atropine in selected wells.

The inhibition of [$^3$H]QNB binding by test compounds was determined by including seven different concentrations of the test compound in selected wells. Each concentration was replicated in triplicate. $IC_{50}$ values were estimated as the concentration of compound that inhibited 50 percent of specific [$^3$H]QNB binding. Inhibition constants (Ki values), reported in nM, were calculated from the $IC_{50}$ values using the method of Cheng et al., *Biochem. Pharmacol.* 22: 3099 (1973).

Synthetic Examples

The following synthetic examples are provided to illustrate the present invention, and should not be construed as limiting thereof. In these examples, all parts and percentages are by weight, unless otherwise noted. Unless otherwise indicated, all reagents and solvents were used as obtained from commercial sources, and all reactions were run under a nitrogen atmosphere.

Example 5

Synthesis of 3-(tert-butoxycarbonyl)-3-azabicyclo [3.3.0]octane-7-carboxylic acid The intermediate, 3-(tert-butoxycarbonyl)-3-azabicyclo [3.3.0]octane-7-carboxylic acid, was synthesized using the following procedures.

Diethyl 3-(tert-butoxycarbonyl)-3-azabicyclo[3.3.0] octane-7,7-dicarboxylate

Following the method of Flynn and Zabrowski, *J. Org. Chem.* 55: 3673-3674 (1990), such reference herein incorporated by reference with regard to such synthetic teaching, diethyl allylmalonate (18.0 g, 90.0 mmol) was dissolved in tetrahydrofuran (THF) (50 mL). Sodium hydride (11.5 g, 288 mmol, 60% dispersion in oil) was added to the reaction. After 30 min of stirring at ambient temperature, a solution of N-iodosuccinimide (21.9 g, 97.2 mmol) in THF (100 mL) was added, and the reaction was stirred in the dark at ambient temperature for 15 min. The reaction was poured onto 100 g of silica gel. The contents were diluted with 400 mL of ether and stirred with a glass rod. The contents were then filtered through a bed of silica gel (100 g) in a sintered funnel. The silica gel was washed with ether (4×400 mL). The combined filtrates were concentrated by rotary evaporation to give diethyl 2-allyl-2-iodomalonate, as a yellowish orange liquid, that was used immediately in the next reaction.

The diethyl 2-allyl-2-iodomalonate and N-(tert-butoxycarbonyl)allylamine (20.8 g, 132 mmol) were dissolved in benzene (300 mL). Bis(tributyltin) (3.6 mL, 7.1 mmol) was added to the reaction, and the reaction was exposed to a sunlamp (GE, 275 W) for 35 min. The light source was removed, diisopropylethylamine (100 mL) was added to the reaction, and the mixture was heated at reflux overnight. The reaction mixture was cooled to ambient temperature, washed with water (200 mL), dried (anhydrous sodium sulfate), concentrated (rotary evaporation) and purified by silica gel column chromatography, to obtain 13.0 g (40.6% from diethyl allylmalonate) of diethyl 3-(tert-butoxycarbonyl)-3-azabicyclo[3.3.0]octane-7,7-dicarboxylate as an oil.

3-(tert-Butoxycarbonyl)-3-azabicyclo[3.3.0]octane-7-carboxylic acid

To the diethyl 3-(tert-butoxycarbonyl)-3-azabicyclo[3.3.0]octane-7,7-dicarboxylate (10.5 g, 29.5 mmol) was added water (25 mL) and concentrated (12 N) hydrochloric acid (75 mL). The mixture was heated at reflux for 8 h. The volatiles were evaporated, and the residue was dissolved in water (10 mL) and the pH of the solution was adjusted to pH 8 with 10% aqueous sodium bicarbonate. Di-tert-butyl dicarbonate (8.5 g, 39 mmol) in tert-butanol (60 mL) was added and the reaction was stirred overnight at ambient temperature. Ethyl acetate (100 mL) was added to the reaction and the pH of the solution was adjusted to pH 3 with 2 M aqueous hydrochloric acid. The aqueous layer was extracted with ethyl acetate (200 mL). The organic layer was washed with water (2×200 mL) and brine (100 mL), dried (anhydrous sodium sulfate), concentrated (rotary evaporation), and purified by silica gel column chromatography to give 5.1 g of 3-(tert-butoxycarbonyl)-3-azabicyclo[3.3.0]octane-7-carboxylic acid, as a white solid ($^1$H NMR (CDCl$_3$, 300 MHz): δ 3.59-3.40 (m, 2H), 3.36-3.05 (m, 2H), 3.02-2.76 (m, 2H), 2.65-2.60 (m, 1H), 2.24-2.04 (m, 2H), 1.85-1.66 (m, 2H), 1.46 (s, 9H); MS (m/z): 256 (M+1), 200 (M+1-56)).

Example 6

Synthesis of N-methoxy-N-methyl-3-(tert-butoxycarbonyl)-3-azabicyclo[3.3.0]octane-7-carboxamide To a mixture of 3-(tert-butoxycarbonyl)-3-azabicyclo[3.3.0]octane-7-carboxylic acid (0.930 g, 3.65 mmol), N,O-dimethylhydroxylamine hydrochloride (0.71 g, 7.3 mmol) and diisopropylethylamine (DIPEA) (3.24 mL, 18.3 mmol) in N,N-dimethylformamide (DMF) (50 mL) was added O-(benzotriazol-1-yl)-N,N,N',N'-tetramethyluronium hexafluorophosphate (HBTU) (2.07 g, 5.48 mmol), and the mixture was stirred at ambient temperature overnight. The reaction was poured into saturated aqueous sodium bicarbonate (100 mL) and extracted with ethyl acetate (100 mL). The organic layer was washed with water (200 mL), dried over anhydrous sodium sulfate, concentrated by rotary evaporation and purified by silica gel flash column chromatography, to obtain 0.94 g (86% yield) of the N-methoxy-N-methyl-3-(tert-butoxycarbonyl)-3-azabicyclo[3.3.0]octane-7-carboxamide, as an oil ($^1$H NMR (CDCl$_3$, 300 MHz): δ 3.69 (s, 3H), 3.6-3.42 (m, 2H), 3.36-3.05 (m, 3H), 3.18 (s, 3H), 2.82-2.57 (m, 2H), 2.08-2.02 (m, 2H), 1.82-1.65 (m, 2H), 1.46 (d, 9H); MS (m/z: 299 (M+1), 243 (M+1-56)).

Example 7

Ketone derivatives of 3-azabicyclo[3.3.0]octane-7-carboxylic acid

Method A: Certain acyl (ketone) analogs of 3-azabicyclo[3.3.0]octane can be prepared from 3-azabicyclo[3.3.0]octane-7-carboxylic acid, through the reaction of the N-methoxy-N-methyl-3-(tert-butoxycarbonyl)-3-azabicyclo[3.3.0]octane-7-carboxamide derivative with aryl- and alkyllithium reagents. The following procedure is exemplary.

2-Furanyl(3-azabicyclo[3.3.0]oct-7-yl)methanone trifluoroacetate

A solution of 2-bromofuran (0.295 g, 2.00 mmol) in THF (15 mL) at −78° C. was treated with n-butyllithium (n-BuLi) solution (2.5 M solution in hexanes, 0.85 mL, 2.1 mmol), and the mixture was stirred for 1 h. A solution of N-methoxy-N-methyl-3-(tert-butoxycarbonyl)-3-azabicyclo[3.3.0]octane-7-carboxamide (0.60 g, 2.0 mmol) in THF (3 mL) was added, and the mixture was warmed to ambient temperature over 8 h. The reaction was quenched with water (0.5 mL), diluted with ethyl acetate (20 mL), dried over anhydrous sodium sulfate and concentrated. The residue was purified on a silica gel column, eluting with an ethyl acetate in hexane gradient, to obtain samples of the trans isomer (the acyl group trans to the pyrrolidine ring) (0.12 g, first eluting), the cis isomer (the acyl group cis to the pyrrolidine ring) (0.17 g, second eluting) and a mixture of isomers (0.1 g), accounting for the total yield of 62%. The separated samples were de-protected and converted into their trifluoroacetate salts by reaction with trifluoroacetic acid (TFA) in dichloromethane (5 mL), followed by purification by HPLC using acetonitrile and 0.05% aqueous TFA as mobile phase, to give trans-2-furanyl(3-azabicyclo[3.3.0]oct-7-yl)methanone trifluoroacetate (0.065 g), cis-2-furanyl(3-azabicyclo[3.3.0]oct-7-yl)methanone trifluoroacetate (0.106 g) and a mixture of cis and trans isomers (0.075 g) ($^1$H NMR of trans isomer (CD$_3$OD, 300 MHz): δ 7.81 (dd, J=1.71, 0.73 Hz, 1H), 7.43 (dd, J=3.42, 0.73 Hz, 1H), 6.66 (dd, J=3.66, 1.71 Hz, 1H), 3.89-3.78 (m, 1H), 3.58-3.47 (m, 2H), 3.28-2.95 (m, 4H), 2.19-2.10 (m, 2H), 1.94-1.85 (m, 2H); MS (m/z): 206 (M+1); $^1$H NMR of cis isomer (CD$_3$OD, 300 MHz): δ 7.81 (dd, J=1.71, 0.73 Hz, 1H), 7.43 (dd, J=3.66, 0.73 Hz, 1H), 6.66 (dd, J=3.66, 1.71 Hz, 1H), 3.83-3.72 (m, 1H), 3.39-3.32 (m, 2H), 3.25-3.19 (m, 2H), 3.07-2.98 (m, 2H), 2.39-2.28 (m, 2H), 1.81-1.70 (m, 2H); MS (m/z): 206 (M+1)).

Procedures similar to the above were used to make a variety of acyl (ketone) derivatives, including the compounds in Table 1. In some cases, the cis/trans isomers were chromatographically separated, and in others they were not.

TABLE 1

| Structure | Name | Rat α4β2 Ki | Human α4β2 Ki | α7 Ki | MS: m/z (M + H) | ¹H NMR: CD$_3$OD, 300 MHz, δ |
|---|---|---|---|---|---|---|
| 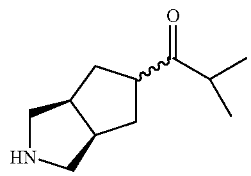 | 1-(3-azabicyclo[3.3.0]oct-7-yl)-2-methyl-1-propanone | 0.3 | 0.2 | 2377.4 | 182 | 3.57-3.44 (m, 1H), 3.39-3.18 (m, 2H), 3.00-2.93 (m, 4H), 2.84-2.72 (m, 1H), 2.28-2.19 and 2.06-1.94 (m, 2H), 1.82-1.73 and 1.61-1.50 (m, 2H), 1.08-1.06 (m, 6H). |
| 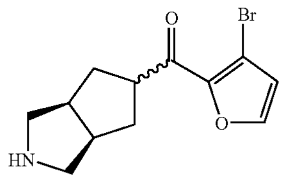 | 3-bromofuran-2-yl(3-azabicyclo[3.3.0]oct-7-yl)methanone | 2.8 | 0.9 | ND; failed HTS | 284, 286 | |
| 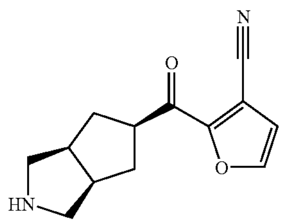 | cis-3-cyanofuran-2-yl(3-azabicyclo[3.3.0]oct-7-yl)methanone | 14 | 25.7 | ND; failed HTS | 231 | |
| 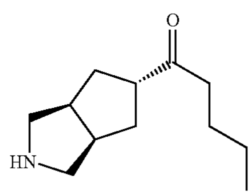 | trans-1-(3-azabicyclo[3.3.0]oct-7-yl)-1-pentanone | 108 | 186.4 | ND; failed HTS | 196 | |
| 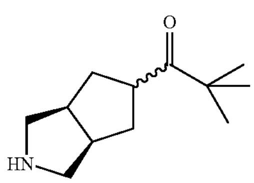 | 1-(3-azabicyclo[3.3.0]oct-7-yl)-2,2-dimethyl-1-propanone | 21.4 | 4.2 | ND; failed HTS | 196 | |
| 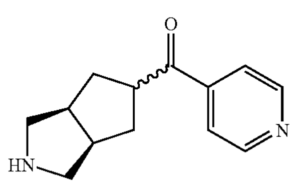 | pyridin-4-yl(3-azabicyclo[3.3.0]oct-7-yl)methanone | 43 | 36.4 | ND; failed HTS | 217 | |
| 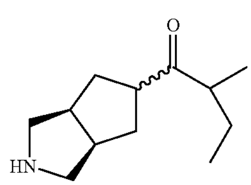 | 1-(3-azabicyclo[3.3.0]oct-7-yl)-2-methyl-1-butanone | 11.1 | 3.3 | ND; failed HTS | 196 | |
| 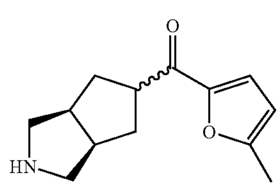 | 5-methylfuran-2-yl(3-azabicyclo[3.3.0]oct-7-yl)methanone | 74.3 | 37 | ND; failed HTS | 220 | |

TABLE 1-continued

| Structure | Name | Rat α4β2 Ki | Human α4β2 Ki | α7 Ki | MS: m/z (M + H) | ¹H NMR: CD₃OD, 300 MHz, δ |
|---|---|---|---|---|---|---|
| 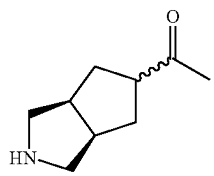 | 1-(3-azabicyclo[3.3.0]oct-7-yl)-1-ethanone | 7.3 | 10.7 | >10,000 | 154 | |
| 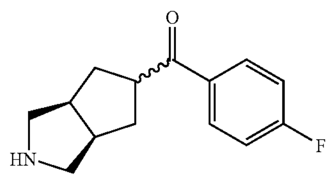 | 4-fluorophenyl(3-azabicyclo[3.3.0]oct-7-yl)methanone | 321.5 | 134.3 | ND; failed HTS | 234 | |
| 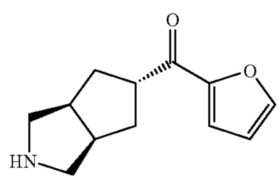 | trans-2-furanyl(3-azabicyclo[3.3.0]oct-7-yl)methanone | 462.8 | 225.7 | ND; failed HTS | 206 | |
| 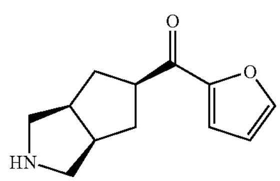 | cis-2-furanyl(3-azabicyclo[3.3.0]oct-7-yl)methanone | 11 | 13.2 | ND; failed HTS | 206 | |

Method B: Certain other acyl derivatives (ketones) can be prepared by reaction of N-methoxy-N-methyl-3-(tert-butoxycarbonyl)-3-azabicyclo[3.3.0]octane-7-carboxamide with alkylmagnesium halide reagents (Grignard reagents). The following procedure is exemplary.

Cyclopropyl(3-azabicyclo[3.3.0]oct-7-yl)methanone trifluoroacetate

To a solution of N-methoxy-N-methyl-3-(tert-butoxycarbonyl)-3-azabicyclo[3.3.0]octane-7-carboxamide (0.20 g, 0.67 mmol) in THF (4.0 mL) at 0° C. was added a solution of cyclopropylmagnesium bromide (0.50 M solution in ether, 5.4 mL, 2.7 mmol), and the reaction was stirred overnight at ambient temperature. The reaction was quenched with 2% aqueous acetic acid (10 mL), and the aqueous phase was extracted with ethyl acetate (20 mL). The organic extracts were dried (anhydrous sodium sulfate), concentrated and purified by silica gel column chromatography, eluting with an ethyl acetate in hexane gradient, to obtain two pure cis (late eluting) and trans (early eluting) isomers (0.06 g and 0.07 g, respectively) (69% total yield). The separated isomers were de-protected and converted into their trifluoroacetate salts by reaction with trifluoroacetic acid in dichloromethane (5 mL), followed by purification by HPLC using acetonitrile and 0.05% aqueous TFA as mobile phase, to give trans-cyclopropyl(3-azabicyclo[3.3.0]oct-7-yl)methanone trifluoroacetate (0.026 g), cis-cyclopropyl(3-azabicyclo[3.3.0]oct-7-yl)methanone trifluoroacetate (0.023 g), as oils (¹H NMR of trans isomer (CD₃OD, 300 MHz): δ 3.59-3.40 (m, 2H), 3.37-3.29 (m, 1H), 3.02-2.90 (m, 4H), 2.16-2.03 (m, 3H), 1.87-1.80 (m, 2H), 0.96-0.91 (m, 4H); MS (m/z): 180 (M+1); ¹H NMR of cis isomer (CD₃OD, 300 MHz): δ 3.38-3.21 (m, 3H), 3.18-3.14 (m, 2H), 3.04-2.94 (m, 2H), 2.38-2.23 (m, 2H), 2.15-2.07 (m, 1H), 1.72-1.61 (m, 2H), 0.97-0.91 (m, 4H); MS (m/z): 180 (M+1)).

Procedures similar to the above were used to make a variety of acyl (ketone) derivatives, including the compounds in Table 2. Typically the cis/trans isomers were not separated.

TABLE 2

| Structure | Name | Rat α4β2 Ki | Human α4β2 Ki | α7 Ki | MS: m/z (M + H) |
|---|---|---|---|---|---|
| (structure) | trans-1-(3-azabicyclo[3.3.0]oct-7-yl)-2-buten-1-one | 15.4 | 29.7 | >10,000 | 180 |
| (structure) | cyclopentyl(3-azabicyclo[3.3.0]oct-7-yl)methanone | 15.9 | 7.5 | ND; failed HTS | 208 |
| (structure) | cyclohexyl(3-azabicyclo[3.3.0]oct-7-yl)methanone | 192.4 | 44.2 | ND; failed HTS | 222 |
| (structure) | 1-(3-azabicyclo[3.3.0]oct-7-yl)-3-methyl-1-butanone | 27.3 | 4.6 | ND; failed HTS | 196 |

Method C: Certain acyl derivatives (ketones) can be prepared by reaction of 3-(tert-butoxycarbonyl)-3-azabicyclo[3.3.0]octane-7-carboxylic acid chloride with trimethylsilyldiazomethane, followed by subsequent transformations. The following procedures are exemplary.

1-(3-(tert-Butoxycarbonyl)-3-azabicyclo[3.3.0]oct-7-yl)-2-bromo-1-ethanone

To a solution of 3-(tert-butoxycarbonyl)-3-azabicyclo[3.3.0]octane-7-carboxylic acid (0.580 g, 2.27 mmol) in dichloromethane (10 mL) was added oxalyl chloride (1.45 g, 11.4 mmol) and a drop of DMF. The reaction was stirred at ambient temperature for 2 h. The volatiles were evaporated, and the acid chloride was dissolved in ether-acetonitrile (20 mL, 9:1). A solution of trimethylsilyldiazomethane (2.0 M solution in hexanes, 3.5 mL, 7.0 mmol) was added, and the reaction was stirred overnight at ambient temperature. The reaction mixture was concentrated in vacuo, and the resulting yellow oil was dissolved in ether (20 mL). Aqueous hydrobromic acid (47%, 1.0 mL) was quickly added with vigorous stirring. After 1 min, the reaction was quenched with solid sodium bicarbonate (1.0 g), and the mixture was stirred for 15 min. The reaction mixture was filtered, and the filtrate was concentrated and purified by silica gel column chromatography, eluting with 20-30% ethyl acetate in hexanes, to afford 0.54 g (74% yield) of 1-(3-(tert-butoxycarbonyl)-3-azabicyclo[3.3.0]oct-7-yl)-2-bromo-1-ethanone, as an oil (cis/trans mixture) ($^1$H NMR (CDCl$_3$, 300 MHz): δ 3.94 and 3.92 (s, 2H), 3.58-3.10 (m, 5H), 2.82-2.63 (m, 2H), 2.23-2.00 (m, 2H), 1.84-1.62 (m, 2H), 1.45 and 1.44 (s, 9H). MS (m/z): 332 (M+H), 334 (M+H+2)).

1-(3-Azabicyclo[3.3.0]oct-7-yl)-2-fluoro-1-ethanone trifluoroacetate

A mixture of 1-(3-(tert-butoxycarbonyl)-3-azabicyclo[3.3.0]oct-7-yl)-2-bromo-1-ethanone (0.126 g, 0.380 mmol), potassium fluoride (0.067 g, 1.15 mmol) and 18-crown-6 (0.050 g, 0.19 mmol) in benzene (10 mL) was heated at reflux overnight. The mixture was filtered, and the filtrate was concentrated and purified by silica gel column chromatography, eluting with 20-30% ethyl acetate in hexanes, to obtain the cis isomer (0.022 g), trans isomer (0.030 g), and a mixture of cis/trans 1-(3-(tert-butoxycarbonyl)-3-azabicyclo[3.3.0]oct-7-yl)-2-fluoro-1-ethanone (0.040 g), as oils. The separated isomers were de-protected and converted into their trifluoroacetate salts by reaction with trifluoroacetic acid in dichloromethane (5 mL) (ambient temperature, 1 h). The solvent was evaporated, and the products were dried by vacuum to obtain 1-(3-azabicyclo[3.3.0]oct-7-yl)-2-fluoro-1-ethanone trifluoroacetate as cis and trans isomers (0.025 g and 0.032 g, respectively) ($^1$H NMR of trans isomer (CD$_3$OD, 300 MHz): δ 5.08 (s, 1H), 4.93 (s, 1H), 3.37-3.29 (m, 2H), 3.24-3.16 (m, 3H), 3.00-2.95 9m, 2H), 2.34-2.22 (m, 2H), 1.69-1.58 (m, 2H); MS (m/z): 172 (M+1); $^1$H-NMR of cis isomer (CD$_3$OD, 300 MHz): δ 5.13 (s, 1H), 4.98 (s, 1H), 3.60-3.52 (m, 2H), 3.78-3.67 (m, 2H), 3.12-2.96 (m, 3H), 2.38-2.15 (m, 2H), 1.91-1.64 (m, 2H); MS (m/z): 172 (M+1)). The cis isomer exhibited Ki values at rat and human α4β2 of 6.8 nM and 6.3 nM respectively and did not pass HTS for α7. The trans isomer exhibited a Ki value at rat and human α4β2 of 154 nM and 176 nM respectively and exhibited a Ki value at α7 of >10.000 nM.

1-(3-Azabicyclo[3.3.0]oct-7-yl)-2-methoxy-1-ethanone trifluoroacetate

A mixture of 1-(3-(tert-butoxycarbonyl)-3-azabicyclo[3.3.0]oct-7-yl)-2-bromo-1-ethanone (0.126 g, 0.360 mmol), silver trifluoromethanesulfonate (0.10 g, 0.39 mmol), and silver carbonate (0.10 g, 0.36 mmol) in methanol (4.0 mL) was stirred in the dark for 2 days at ambient temperature. The reaction was filtered, and the filtrate was concentrated and purified by silica gel column chromatography, eluting with 30-40% ethyl acetate in hexanes, to obtain 0.062 g (61% yield) of 1-(3-(tert-butoxycarbonyl)-3-azabicyclo[3.3.0]oct-7-yl)-2-methoxy-1-ethanone as an oil. This was dissolved in dichloromethane (2.0 mL), treated with TFA (0.5 mL), and was stirred at ambient temperature for 2 h. The volatiles were evaporated, and the residue was vacuum dried to obtain 0.045 g of 1-(3-azabicyclo[3.3.0]oct-7-yl)-2-methoxy-1-ethanone trifluoroacetate, as an off-white solid (mixture of cis and trans isomers) ($^1$H NMR (CD$_3$OD, 300 MHz): δ 4.17 (s, 2H), 3.39 (s, 3H), 3.36-3.30 (m, 2H), 3.19-3.12 (m, 3H), 3.00-2.91 (m, 2H), 2.30-2.20 (m, 2H), 1.64-1.75 (m, 2H); MS (m/z): 184 (M+1)). This material exhibited Ki values at rat and human α4β2 of 32 nM and 31 nM respectively and did not pass HIS for α7.

1-(3-Azabicyclo[3.3.0]oct-7-yl)-2-isopropoxy-1-ethanone trifluoroacetate 1-(3-Azabicyclo[3.3.0]oct-7-yl)-2-isopropoxy-1-ethanone trifluoroacetate was prepared from 1-(3-(tert-butoxycarbonyl)-3-azabicyclo[3.3.0]oct-7-yl)-2-bromo-1-ethanone (0.087 g, 0.27 mmol) and isopropanol, according to the procedure described above for the preparation of 1-(3-azabicyclo[3.3.0]oct-7-yl)-2-methoxy-1-ethanone trifluoroacetate, to give a mixture of cis and trans isomers ($^1$H NMR (CD3OD, 300 MHz): δ 4.21 and 4.20 (s, 2H), 3.64 (heptet, J=6.1 Hz) 1H), 3.54-3.42 (m, 1H), 3.24-3.15 (m, 2H), 2.98-2.90 (m, 4H), 2.37-2.22 and 2.06-1.99 (m, 2H), 1.82-1.75 and 1.65-1.54 (m, 2H), 1.18 (d, J=6.1 Hz, 6H); MS (m/z): 212 (M+1)). This material exhibited Ki values at rat and human α4β2 of 427 nM and 261 nM respectively and did not pass HTS for α7.

Example 8

Ester derivatives of 3-azabicyclo[3.3.0]octane-7-carboxylic acid

Method A: Certain ester derivatives of 3-azabicyclo[3.3.0]octane-7-carboxylic acid can be made directly from the N-protected acid, using coupling agents such as dicyclohexylcarbodiimide (DCC). The following procedure is exemplary.

Trifluoroacetate salt of 2,2,2-trifluoroethyl 3-azabicyclo[3.3.0]octane-7-carboxylate A mixture of 3-(tert-butoxycarbonyl)-3-azabicyclo[3.3.0]octane-7-carboxylic acid (0.150 g, 0.588 mmol), 2,2,2-trifluoroethanol (0.118 g, 1.18 mmol), 4-N,N-dimethylaminopyridine (DMAP) (0.143 g, 1.18 mmol) and polymer supported dicyclohexylcarbodiimide (PS-DCC) (0.8 g, loading 3.2 mmol/g) in dichloromethane (20 mL) was stirred at ambient temperature overnight. The reaction mixture was filtered, and the filtrate was concentrated. The residue was purified by HPLC, using acetonitrile and 0.05% aqueous TFA as mobile phase, to obtain 0.053 g (27% yield) of 2,2,2-trifluoroethyl 3-(tert-butoxycarbonyl)-3-azabicyclo[3.3.0]octane-7-carboxylate as an oil ($^1$H NMR (CDCl$_3$, 300 MHz): δ 4.48 (q, J=8.30 Hz, 2H), 3.58-3.46 (m, 2H), 3.26-2.92 (m, 4H), 2.82-2.63 (m, 1H), 2.28-2.07 (m, 2H, 1.84-1.65 (m, 2H), 1.45 (s, 9H); MS (m/z): 338 (M+1), 282 (M+1-56)). The 2,2,2-trifluoroethyl 3-(tert-butoxycarbonyl)-3-azabicyclo[3.3.0]octane-7-carboxylate was dissolved in dichloromethane (5.0 mL), treated with TFA (2.0 mL), and the reaction was stirred at ambient temperature for 1 h. The solvent was evaporated and the crude product was purified on HPLC, using acetonitrile and 0.05% TFA in water as mobile phase, to obtain 0.023 g of the trifluoroacetate salt of 2,2,2-trifluoroethyl 3-azabicyclo[3.3.0]octane-7-carboxylate (as a cis/trans mixture) as an oil ($^1$H NMR (CD$_3$OD, 300 MHz): δ 4.62 (q, J=8.79 Hz, 2H), 3.64-3.42 (m, 1H), 3.3.38-3.32 (m, 1H), 3.22-3.05 (m, 2H), 3.02-2.95 (m, 3H), 2.42-2.07 (m, 2H), 1.96-1.63 (m, 2H); MS (m/z): 238 (M+1)).

Procedures similar to the above were used to make a variety of ester derivatives, including the compounds in Table 3. Typically, the cis/trans isomers were not separated.

TABLE 3

| Structure | Name | Rat α4β2 Ki | Human α4β2 Ki | α7 Ki | MS: m/z (M + H) | $^1$H NMR: CD$_3$OD, 300 MHz, δ |
|---|---|---|---|---|---|---|
| 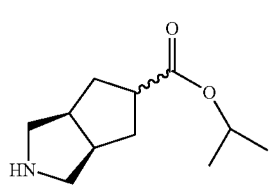 | isopropyl 3-azabicyclo[3.3.0]octane-7-carboxylate | 102.7 | 7.8 | >10,000 | 198 | 5.02-4.93 (m, 1 H), 3.38-3.31 (m, 2H), 3.22-3.18 (m, 2H), 3.0-2.81 (m, 3H), 2.33-2.23 and 2.12-2.01 (m, 2H), 1.84-1.77 and 1.71-1.60 (m, 2H), 1.23-1.21 (m, 6H). |
| 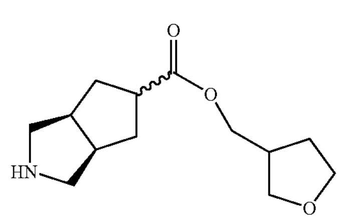 | (tetrahydrofuran-3-yl)methyl 3-azabicyclo[3.3.0]octane-7-carboxylate | 111.1 | 47.7 | ND; failed HTS | 240 |  |

TABLE 3-continued

| Structure | Name | Rat α4β2 Ki | Human α4β2 Ki | α7 Ki | MS: m/z (M + H) | 1H NMR: CD3OD, 300 MHz, δ |
|---|---|---|---|---|---|---|
| 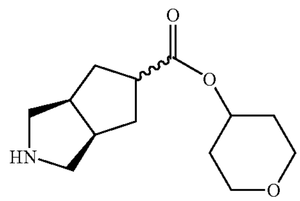 | tetrahydropyran-4-yl 3-azabicyclo[3.3.0]octane-7-carboxylate | 68.5 | 146.5 | ND; failed HTS | 240 |  |
| 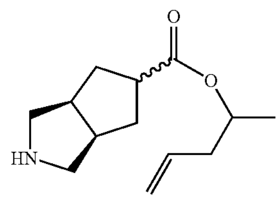 | pent-4-en-2-yl 3-azabicyclo[3.3.0]octane-7-carboxylate | ND | 44.8 | >10,000 | 224 |  |
| 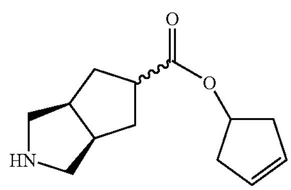 | cyclopent-3-en-1-yl 3-azabicyclo[3.3.0]octane-7-carboxylate | 59.3 | 22.5 | >10,000 | 222 |  |
| 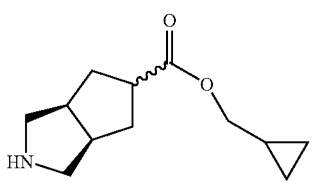 | cyclopropylmethyl 3-azabicyclo[3.3.0]octane-7-carboxylate | 62.1 | 40.3 | >10,000 | 210 |  |
| 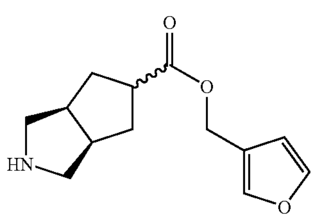 | (furan-3-yl)methyl 3-azabicyclo[3.3.0]octane-7-carboxylate | 19.6 | 16.3 | ND; failed HTS | 236 |  |
| 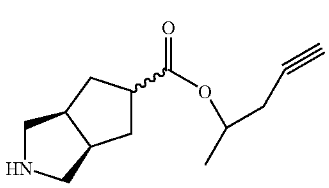 | pent-4-yn-2-yl 3-azabicyclo[3.3.0]octane-7-carboxylate | 144.2 | 68.7 | ND; failed HTS | 222 |  |
| 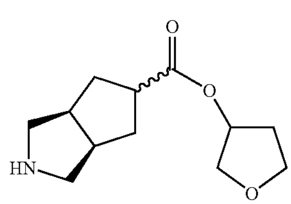 | tetrahydrofuran-3-yl 3-azabicyolo[3.3.0]octane-7-carboxylate | 128.6 | 119.8 | >10,000 | 226 |  |

TABLE 3-continued

| Structure | Name | Rat α4β2 Ki | Human α4β2 Ki | α7 Ki | MS: m/z (M + H) | ¹H NMR: CD₃OD, 300 MHz, δ |
|---|---|---|---|---|---|---|
| 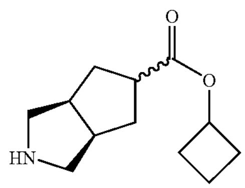 | cyclobutyl 3-azabicyclo[3.3.0]octane-7-carboxylate | ND | 80.6 | >10,000 | 210 | |
| 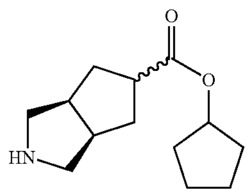 | cyclopentyl 3-azabicyclo[3.3.0]octane-7-carboxylate | 26.6 | 13.9 | ND; failed HTS | 224 | |
| 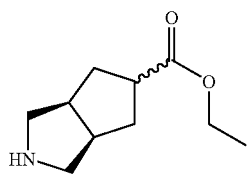 | ethyl 3-azabicyclo[3.3.0]octane-7-carboxylate | 45.8 | 17.5 | ND; failed HTS | 184 | 4.16-4.09 (m, 2H), 3.57-3.42 (m, 1H), 3.35-3.29 (m, 1H), 3.20-3.16 (m, 2H), 3.02-2.83 (m, 3H), 2.37-2.23 and 2.15-2.02 (m, 2H), 1.84-1.79 and 1.76-1.60 (m, 2H), 1.24 (t, J = 7.08 Hz, 3H). |
| 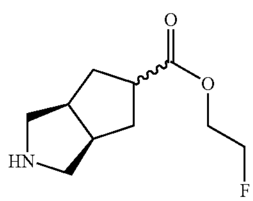 | 2-fluoroethyl 3-azabicyclo[3.3.0]octane-7-carboxylate | 55.1 | 102.1 | ND; failed HTS | 202 | |
| 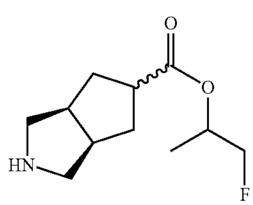 | 1-fluoroprop-2-yl 3-azabicyclo[3.3.0]octane-7-carboxylate | 270.8 | 111.8 | ND; failed HTS | 216 | |

Method B: The methyl ester of 3-azabicyclo[3.3.0]octane-7-carboxylic acid was made by a different procedure, which follows.

Hydrochloride salt of methyl 3-azabyclo[3.3.0]octane-7-carboxylate

To a solution of 3-(tert-butoxycarbonyl)-3-azabicyclo[3.3.0]octane-7-carboxylic acid (0.15 g, 0.59 mmol) in methanol (5 mL) at 0° C. was added a solution of trimethylsilyldiazomethane (~4.0 mL, 2 M solution in hexanes) until the yellow color persisted. After 5 min, a drop of acetic acid was added and the reaction mixture was concentrated to give an oil (0.152 g). This ester was dissolved in ethyl acetate (4.0 mL), and 4 M hydrochloric acid in 1,4-dioxane (1.0 mL) was added. The reaction was stirred overnight at ambient temperature. The resulting solid was collected by filtration, washed with ethyl acetate (10 mL) and dried in vacuo, to obtain 0.11 g (91% yield) of the hydrochloride salt of methyl 3-azabyclo[3.3.0]octane-7-carboxylate (as a cis/trans mixture), as a white fluffy solid (¹H NMR (CD₃OD, 300 MHz): δ 3.74 (s, 3H), 3.57-3.32 (m, 2H), 3.222-3.16 (m, 2H), 3.05-2.88 (m, 3H), 2.38-2.03 (m, 2H), 1.83-1.61 (m, 2H); MS (m/z): 170 (M+1)). This material exhibited Ki values at rat and human α4β2 of 20 nM and 8 nM respectively and a Ki value at α7 of >10,000 nM.

Example 9

Amide derivatives of 3-azabicyclo[3.3.0]octane-7-carboxylic acid

Certain amide derivatives of 3-azabicyclo[3.3.0]octane-7-carboxylic acid can be produced through the intermediacy of the acid chloride. The following procedure is exemplary.

N-(2,2,2-Trifluoroethyl)-3-azabicyclo[3.3.0]octane-7-carboxamide trifluoroacetate To a solution of 3-(tert-butoxycarbonyl)-3-azabicyclo[3.3.0]octane-7-carboxylic acid (0.100 g, 0.392 mmol) in dichloromethane (5 mL) were added oxalyl chloride (0.250 g, 1.96 mmol) and a drop of DMF, and the mixture was stirred at ambient temperature for 2 h. The solvent was evaporated and the residue (acid chloride) was vacuum dried. To the acid chloride in acetonitrile (5 mL) were added DIPEA (0.200 mL, 1.15 mmol) and 2,2,2-trifluoroethylamine (0.080 g, 0.081 mmol), and the mixture was stirred overnight at ambient temperature. The solvent was evaporated, and the crude amide was purified by silica gel column chromatography, eluting with an ethyl acetate in hexane gradient, to obtain 0.075 g of N-(2,2,2-trifluoroethyl)-3-(tert-butoxycarbonyl)-3-azabicyclo[3.3.0]octane-7-carboxamide (mixture of cis and trans isomers) as an oil. The majority of this sample (0.065 g, 0.19 mmol) was dissolved in dichloromethane (3 mL), combined with TFA (2 mL), and stirred at ambient temperature for 1 h. The solvent was evaporated, and the residue was purified by HPLC, using acetonitrile and 0.05% aqueous TFA as the mobile phase, to obtain 0.050 g of N-(2,2,2-trifluoroethyl)-3-azabicyclo[3.3.0]octane-7-carboxamide trifluoroacetate (as a mixture of cis and trans isomers), as an oil ($^1$H NMR (CD$_3$OD, 300 MHz): δ 3.93 (q, J=9.28 Hz, 2H), 3.38-3.21 (m, 4H), 3.02-2.80 (m, 3H), 2.32-2.22 (m, 2H), 1.74-1.62 (m, 2H); MS (m/z): 238 (M+1)). This material exhibited a Ki value at human α4β2 of 261 nM and did not pass HIS for α7.

Procedures similar to the above were used to make a variety of amide derivatives, including the compounds in Table 4. In some cases cis and trans isomers were chromatographically separated, in many cases they were not.

TABLE 4

| Structure | Name | Rat α4β2 Ki | Human α4β2 Ki | α7 Ki | MS: m/z (M + H) | $^1$H NMR: CD$_3$OD, 300 MHz, δ |
|---|---|---|---|---|---|---|
| 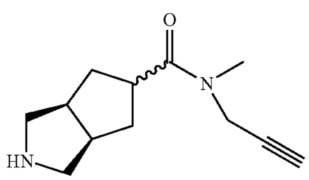 | N-methyl-N-prapargyl-3-azabicyclo[3.3.0]octane-7-carboxamide | 138.7 | 52.5 | 10000 | 207 | |
| 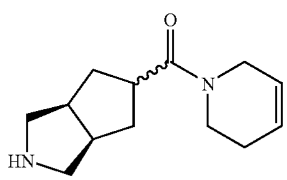 | (3-azabicyclo[3.3.0]oct-7-yl)(2,3,6-trihydropyridin-1-yl)methanone | 46.3 | 28.4 | ND; failed HTS | 221 | 5.93-5.84 (m, 1H), 5.76-5.66 (m, 1H), 4.10-3.99 (m, 2H), 3.71-3.65 (m, 2H), 3.37-3.20 (m, 5H), 3.04-2.95 (m, 2H), 2.2.28-2.06 (m, 4H), 1.78-1.63 (m, 2H). |
| 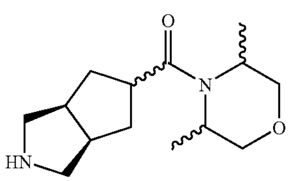 | (3-azabicyclo[3.3.0]oct-7-yl)(2,6-dimethylmorpholin-1-yl)methanone | 57.5 | 71.1 | ND; failed HTS | 253 | |
| 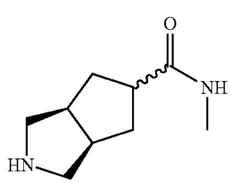 | N-methyl-3-azabicyclo[3.3.0]octane-7-carboxamide | 81.4 | 185 | 27268.1 | 169 | |
| 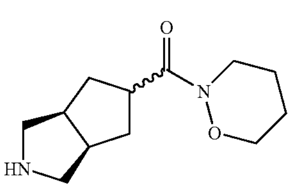 | (3-azabicyclo[3.3.0]oct-7-yl)(1-oxazinan-2-yl)methanone | 17.4 | 5.5 | 10000 | 225 | |
| 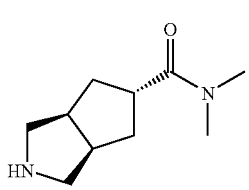 | trans-N,N-dimethyl-3-azabicyclo[3.3.0]octane-7-carboxamide | 28.7 | 113.5 | ND; failed HTS | 183 | 3.30-3.18 (m, 5H), 3.12 (s, 3H), 3.04-2.94 (m, 5H), 2.25 (m, 2H), 1.68 (m, 2H) |

TABLE 4-continued

| Structure | Name | Rat α4β2 Ki | Human α4β2 Ki | α7 Ki | MS: m/z (M + H) | ¹H NMR: CD₃OD, 300 MHz, δ |
|---|---|---|---|---|---|---|
| 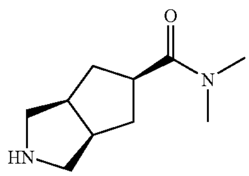 | cis-N,N-dimethyl-3-azabicyclo[3.3.0]octane-7-carboxamide | ND | 1344.3 | ND; failed HTS | 183 | 3.50 (m, 2H), 3.32 (m, 1H), 3.12 (s, 3H), 3.06-2.93 (m, 7H), 2.05 (m, 2H), 1.70 (m, 2H) |
| 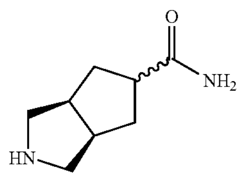 | 3-azabicyclo[3.3.0]octane-7-carboxamide | 393.7 | 319.8 | 8276.1 | 155 | |
| 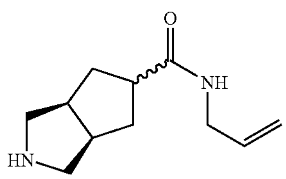 | N-allyl-3-azabicyclo[3.3.0]octane-7-carboxamide | 419.1 | 175.6 | 10000 | 195 | 5.90-5.77 (m, 1H), 5.20-5.08 (m, 2H), 3.81-3.78 (m, 2H), 3.57-3.50 and 3.38-3.22 (m, 4H), 3.07-2.95 (m, 2H), 2.94-2.80 (m, 1H), 2.31-2.21 and 2.08-1.97 (m, 2H), 1.84-1.78 and 1.77-1.63 (m, 2H). |
| 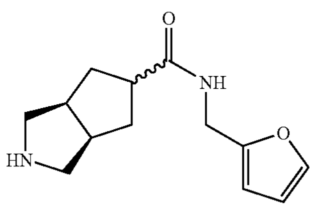 | N-(2-furanylmethyl)-3-azabicyclo[3.3.0]octane-7-carboxamide | 272.2 | 302.1 | 74941.4 | 235 | |
| 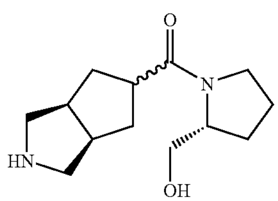 | (R)-(2-(hydroxymethyl)-1-pyrrolidinyl)(3-azabicyclo[3.3.0]oct-7-yl)methanone | 387.1 | 255 | ND; failed HTS | 239 | |
| 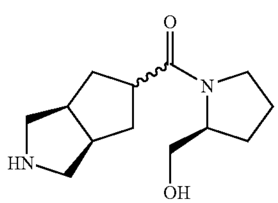 | (S)-(2-(hydroxymethyl)-1-pyrrolidinyl)(3-azabicyclo[3.3.0]oct-7-yl)methanone | 537.5 | 270.7 | ND; failed HTS | 239 | |

Example 10

Derivatives of 3-azabicyclo[3.3.0]oct-6-ene-7-carboxylic acid

Certain unsaturated analogs of 3-azabicyclo[3.3.0]octane-7-carboxylic acid, namely esters, amides and ketone derivatives of 3-azabicyclo[3.3.0]oct-6-ene-7-carboxylic acid, can be produced using techniques exemplified in the following procedures.

Methyl 3-(tert-butoxycarbonyl)-3-azabicyclo[3.3.0]-oct-6-ene-7-carboxylate

To a solution of 3-(tert-butoxycarbonyl)-3-azabicyclo[3.3.0]octan-7-one (4.08 g, 18.1 mmol) (available as described by Dart et al. in PCT WO 04/016604) in THF (50 mL) at −78° C. was added a solution of lithium hexamethyldisilazide (1.00 M solution in THF, 21.8 mL, 21.8 mmol), and the reaction was stirred for 45 min at −78° C. A solution of N-(5-chloropyridin-2-yl)-bis-trifluoromethanesulfonimide (8.53 g, 21.8 mmol) in THF (10 mL) was added and the reaction was warmed to ambient temperature over 1.5 h. The solvent was evaporated, and the product was purified on a flash silica gel column, eluting with 20-30% ethyl acetate in hexanes, to obtain 6.3 g of 3-(tert-butoxycarbonyl)-7-(trifluoromethylsulfonyl)-3-azabicyclo[3.3.0]oct-6-ene, as an oil. This was combined with palladium acetate (0.20 g, 0.88 mmol), triphenylphosphine (0.46 g, 1.8 mmol), and triethylamine (4.94 mL, 35.3 mmol) in DMF-methanol (120 mL, 3:2) and carbon monoxide gas was bubbled through the solution for 15 min. The reaction mixture was stirred under a carbon monoxide atmosphere for 20 h at ambient temperature. Ether (300 mL) was added to the reaction, and the mixture was washed with water (500 mL), followed by 10% aqueous sodium chloride (200 mL). The organic layer was dried (anhydrous sodium sulfate), concentrated (rotary evaporation), and purified by silica gel column chromatography eluting with 10-20% ethyl acetate in hexanes to obtain 3.5 g (72% yield) of methyl 3-(tert-butoxycarbonyl)-3-azabicyclo[3.3.0]-oct-6-ene-7-carboxylate, as an oil ($^1$H NMR (CDCl$_3$, 300 MHz): δ 6.60 (bs, 1H), 3,74 (s, 1H), 3.74-3.61 (m, 1H), 3.58-3.41 (m, 3H), 3.08-2.85 (m, 2H), 2.82-2.74 (m, 1H), 2.50-2.44 (m, 1H), 1.43 (s, 9H); MS (m/z): 268 (M+1), 212 (M+1-56)).

Hydrochloride salt of methyl
3-azabicyclo[3.3.0]-oct-6-ene-7-carboxylate

To a solution of methyl 3-(tert-butoxycarbonyl)-3-azabicyclo[3.3.0]-oct-6-ene-7-carboxylate (0.095 g, 0.36 mmol) in ethyl acetate (2 mL) was added 4 M hydrochloric acid in 1,4-dioxane (2.0 mL), and the reaction was stirred at ambient temperature for 2 h. Ether (20 mL) was added, and the resulting solid was collected by filtration and vacuum dried to give 0.055 (77% yield) of methyl 3-azabicyclo[3.3.0]-oct-6-ene-7-carboxylate hydrochloride, as a white solid ($^1$H NMR (CD3OD, 300 MHz): δ 6.59 (bs, 1H), 3.80-3.74 (m, 1H), 3.74 (s, 3H), 3.52-3.40 (m, 2H), 3.38-3.30 (m, 1H), 3.24-3.18 (m, 1H), 3.12-3.04 (m, 1H), 3.00-2.88 (m, 1H), 2.61-2.50 (m, 1H); MS (m/z): 168 (M+1)). This material exhibited Ki values at rat and human α4β2 of 5 nM and 2 nM respectively and did not pass HIS for α7.

3-(tert-Butoxycarbonyl)-3-azabicyclo[3.3.0]-oct-6-ene-7-carboxylic acid

To a solution of methyl 3-(tert-butoxycarbonyl)-3-azabicyclo[3.3.0]-oct-6-ene-7-carboxylate (0.350 g, 1.31 mmol) in THF-methanol (6.0 mL, 1:1) was added a solution of lithium hydroxide (0.100 g in 1 mL of water, 3.94 mmol), and the reaction was stirred at ambient temperature for 3 h. The solvent was evaporated, the residue was acidified to pH 4 with 1 M aqueous hydrochloric acid, and extracted with ethyl acetate (50 mL). The organic layer was washed with water (50 mL) and brine (50 mL), dried (anhydrous sodium sulfate), and concentrated to obtain 0.31 g (92% yield) of 3-(tert-butoxycarbonyl)-3-azabicyclo[3.3.0]-oct-6-ene-7-carboxylic acid, as a white solid ($^1$H NMR (CDCl$_3$, 300 MHz): δ 6.76 (bs, 1H), 3.76-3.62 (m, 1H), 3.58-3.42 (m, 2H), 3.11-2.94 (m, 2H), 2.84-2.67 (m, 1H), 2.46-2.23 (m, 1H), 1.42 (s, 9H). MS (m/z): 254 (M+1), 198 (M+1-56)).

N-Methoxy-N-methyl-3-azabicyclo[3.3.0]oct-6-ene-7-carboxamide trifluoroacetate

To a solution of 3-(tert-butoxycarbonyl)-3-azabicyclo[3.3.0]-oct-6-ene-7-carboxylic acid (0.080 g, 0.32 mmol) in dichloromethane (3.0 mL) was added oxalyl chloride (0.20 g, 1.6 mmol), followed by a drop of DMF. After stirring for 1 h, the the reaction mixture was concentrated in vacuo, and the residual acid chloride was dissolved in acetonitrile (3.0 mL). DIPEA (0.17 mL, 0.96 mmol) and N,O-dimethylhydroxylamine hydrochloride (0.042 g, 0.43 mmol) were added, and the reaction was stirred at ambient temperature for 1 h. The solvent was evaporated, and the residue was purified by silica gel column chromatography, eluting with 80-90% ethyl acetate in hexanes, to obtain 0.078 g (82% yield) of N-methoxy-N-methyl-3-(tert-butoxycarbonyl)-3-azabicyclo[3.3.0]oct-6-ene-7-carboxamide, as an oil. This was dissolved in dichloromethane (3.0 mL), treated with TFA (2.0 mL) and stirred at ambient temperature for 1 h. The volatiles were evaporated, and the residue was vacuum dried to obtain 0.07 g of N-methoxy-N-methyl-3-azabicyclo[3.3.0]oct-6-ene-7-carboxamide trifluoroacetate, as an oil ($^1$H NMR (CD$_3$OD, 300 MHz): δ 6.29 (bs, 1H), 3.80-3.89 (m, 1H), 3.88 (s, 3H), 3.54-3.41 (m, 2H), 3.38-3.30 (m, 1H), 3.26 (s, 3H), 3.22-3.03 (m, 3H), 2.66-2.59 (m, 1H); MS (m/z): 197 (M+1)).

Certain other amide derivatives of 3-azabicyclo[3.3.0]oct-6-ene-7-carboxylic acid were made using the above procedures. Table 5 list some of those derivatives.

TABLE 5

| Structure | Name | Rat α4β2 Ki | Human α4β2 Ki | α7 Ki | MS: m/z (M + H) |
|---|---|---|---|---|---|
| 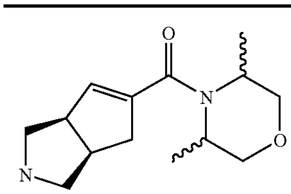 | (3-azabicyclo[3.3.0] oct-6-en-7-yl)(2,6-dimethylmorpholin-1-yl)methanone | ND | 1706.3 | ND, failed HTS | 251 |
| 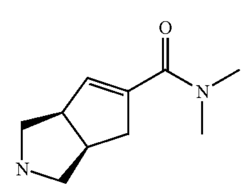 | N,N-dimethyl-3-azabicyclo[3.3.0] oct-6-ene-7-carboxamide | 60 | 163.7 | >10,000 | 181 |

2-Furanyl(3-azabicyclo[3.3.0]oct-6-en-7-yl)methanone trifluoroacetate

To a solution of 2-bromofuran (0.11 g, 0.74 mmol) in THF (3 mL) at −78° C. was added n-BuLi solution (2.5 M solution in hexanes, 0.30 mL, 0.75 mmol) and the mixture was stirred for 1 h. A solution of N-methoxy-N-methyl-3-(tert-butoxycarbonyl)-3-azabicyclo[3.3.0]oct-6-ene-7-carboxamide (0.20 g, 0.65 mmol) in THF (2 mL) was added, and the mixture was warmed to ambient temperature over 8 h. The reaction was quenched with water (0.2 mL), diluted with of ethyl (20 mL) acetate, dried over anhydrous sodium sulfate and concentrated by rotary evaporation. The crude product was purified on silica gel column chromatography to obtain 0.10 g of 2-furanyl(3-(tert-butoxycarbonyl)-3-azabicyclo[3.3.0]oct-6-en-7-yl)methanone and 0.06 g of recovered starting material. A sample of 2-furanyl(3-(tert-butoxycarbonyl)-3-azabicyclo[3.3.0]oct-6-en-7-yl)methanone (0.050 g, 0.16 mmol) was dissolved in dichloromethane (3 mL), treated with TFA (2.0 mL), and stirred at ambient temperature for 1 h. The volatiles were evaporated, and the product was vacuum dried to obtain 0.047 g of 2-furanyl(3-azabicyclo[3.3.0]oct-6-en-7-yl)methanone trifluoroacetate ($^1$H NMR (CD$_3$OD, 300 MHz): δ 7.81-7.80 (m, 1H), 7.38-7.36 (m, 1H), 6.91-6.88 (m, 1H), 6.65 (dd, J=3.66, 1.71 Hz), 3.95-3.86 (m, 1H), 3.56-3.40 (m, 3H), 3.27-3.16 (m, 1H), 3.14-3.02 (m, 2H), 2.77-2.68 (m, 1H); MS (m/z): 204 (M+1)). This material exhibited Ki values at rat and human α4β2 of 8 nM and 2 nM respectively and did not pass HTS for α7.

Example 11

Synthesis of 3-(tert-butoxycarbonyl)-3-azabicyclo[3.3.1]nonane-7-carboxylic acid The key intermediate, 3-(tert-butoxycarbonyl)-3-azabicyclo[3.3.1]nonane-7-carboxylic acid, was synthesized using the following procedures, adapted from Speckamp et al., *Tetrahedron* 27: 3143-56 (1971). Such reference is herein incorporated by reference with regard to such synthetic teaching.

Methyl 3-(tert-butoxycarbonyl)-9-oxo-3-azabicyclo[3.3.1]nonane-7-carboxylate To a solution of tert-butyl 4-oxopiperidine-1-carboxylate (15.2 g, 76.3 mmol) in benzene (200 mL) was added pyrrolidine (13.9 g, 195 mmol). The resulting solution was refluxed with a Dean-Stark trap for 16 h. After removing the solvent by rotary evaporation, the residue was dried on high vacuum and re-dissolved in anhydrous acetonitrile (200 mL). This solution was combined with triethylamine (17.3 g, 170 mmol) and maintained at reflux as methyl 3-bromo-2-(bromomethyl)propanoate (20 g, 77 mmol) was added drop-wise. The reaction was further refluxed for 4 h, cooled to ambient temperature, diluted with water (200 mL) and stirred at ambient temperature for 16 h. The volatile solvents were removed by rotary evaporation, and the residue was partitioned between chloroform and water (200 mL each). The aqueous layer was extracted with chloroform (2×100 mL). The combined organic extracts were dried over anhydrous sodium sulfate and concentrated by rotary evaporation. The residue was purified by flash chromatography, using an ethyl acetate in hexane gradient, to give 15.8 g (69.8% yield) of methyl 3-(tert-butoxycarbonyl)-9-oxo-3-azabicyclo[3.3.1]nonane-7-carboxylate, as a colorless syrup ($^1$H NMR (CDCl$_3$): δ 4.43-4.2 (m, 2H), 3.7 (s, 3H), 3.12-3.0 (m, 2H), 2.55-2.43 (m, 2H), 2.41-2.35 (m, 4H), 1.52 (s, 9H); LC-MS (MH$^+$): 298).

Methyl 3-(tert-butoxycarbonyl)-3-azabicyclo[3.3.1]nonane-7-carboxylate

To a solution of methyl 3-(tert-butoxycarbonyl)-9-oxo-3-azabicyclo[3.3.1]nonane-7-carboxylate (14.76 g, 49.63 mmol), in anhydrous THF (250 mL) was added tosylhydrazine (11.1 g, 59.6 mmol), and the mixture was stirred for 2 h at ambient temperature. The reaction mixture was heated to 65° C., sodium cyanoborohydride (12.5 g, 198 mmol) was added, and the mixture was stirred for 16 h at 65° C. The reaction mixture was cooled to ambient temperature and concentrated by rotary evaporation. The residue was purified by flash silica gel chromatography, using an ethyl acetate in hexane gradient, to give 8.71 g (61.9% yield) of the methyl 3-(tert-butoxycarbonyl)-3-azabicyclo[3.3.1]nonane-7-carboxylate as a colorless solid ($^1$H NMR (CDCl$_3$): δ 3.97-3.8 (m, 2H), 3.65 (s, 3H), 2.85-2.75 (m, 2H), 2.57-2.47 (m, 1H), 2.38-2.20 (m, 2H), 2.0-1.7 (m, 4H), 1.68-1.60 (m, 1H), 1.52-1.41 (m, 1H), 1.41 (s, 9H); LC-MS (MH$^+$): 284).

3-(tert-Butoxycarbonyl)-3-azabicyclo[3.3.1]nonane-7-carboxylic acid

Methyl 3-(tert-butoxycarbonyl)-3-azabicyclo[3.3.1]nonane-7-carboxylate (1.62 g, 5.72 mmol) was dissolved in a 2:1:2 mixture of THF/water/methanol (25 mL), and lithium hydroxide monohydrate (0.721 g, 17.2 mmol) was added. The reaction mixture was stirred at 30° C. for 16 h. The volatile solvents were removed by rotary evaporation, and the residue was acidified with 2 N hydrochloric acid and extracted with ethyl acetate (2×50 mL). The combined organic extracts were washed with brine, dried over anhydrous sodium sulfate and concentrated in vacuo to give 1.53 g (100% crude yield) of 3-(tert-butoxycarbonyl)-3-azabicyclo[3.3.1]nonane-7-carboxylic acid, as a colorless solid ($^1$H NMR (CDCl$_3$): δ 3.95-3.8 (m, 2H), 2.85-2.75 (m, 2H), 2.60-2.47 (m, 1H), 2.20-2.12 (m, 2H), 2.0-1.85 (m, 4H), 1.60-1.70 (m, 2H), 1.41 (s, 9H); (LC-MS (MH$^+$): 270).

Example 12

Amide derivatives of 3-azabicyclo[3.3.1]nonane-7-carboxylic acid

Certain amide derivatives of 3-azabicyclo[3.3.1]nonane-7-carboxylic acid can be produced through the intermediacy of the acid chloride. The following procedure is exemplary.

N-Methyl-3-azabicyclo[3.3.1]nonane-7-carboxamide trifluoroacetate 3-(tert-Butoxycarbonyl)-3-azabicyclo[3.3.1]nonane-7-carboxylic acid (0.10 g, 0.37 mmol) was dissolved in anhydrous dichloromethane (3 mL), and treated with oxalyl chloride (0.23 g, 1.9 mmol). After stirring the reaction mixture for 1 h at ambient temperature, the reaction mixture was concentrated under reduced pressure and the residue was dried under high vacuum. The residue was dissolved in anhydrous THF (5 mL), and the solution was treated with 0.92 mL of methylamine (2 M solution in THF) and stirred for 3 h. The reaction mixture was concentrated in vacuo, and the residue was purified by HPLC to give 24 mg of a colorless syrup. This was dissolved in a 1:1 mixture of anhydrous dichloromethane and TFA (1 mL). After stirring for 1 h at ambient temperature, the reaction mixture was concentrated, and the residue was dried under high vacuum, to give 23 mg (20% overall yield) of N-methyl-3-azabicyclo[3.3.1]nonane-7-carboxamide trifluoroacetate, as a colorless syrup ($^1$H NMR (CD$_3$OD): δ 3.26-3.08 (m, 4H), 2.84-2.78 (m 1H), 2.95 (s, 3H), 2.34-2.18 (m, 4H), 1.85-1.60 (m, 4H); LC-MS (MH$^+$): 182.9). This material exhibited Ki values at rat and human α4β2 of 6 nM and 2 nM respectively and a Ki value at α7 of >10,000 nM.

Procedures similar to the above were used to make a variety of amide derivatives, including the compounds in Table 6.

TABLE 6

| Structure | Name | Rat α4β2 Ki | Human α4β2 Ki | α7 Ki | MS: m/z (M + H) | $^1$H NMR: CD$_3$OD, 300 MHz, δ |
|---|---|---|---|---|---|---|
| 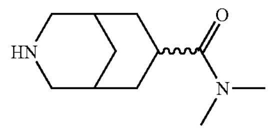 | N,N-dimethyl-3-azabicyclo[3.3.1]nonane-7-carboxamide | 78 | 54 | >10,000 | 197 | |
| 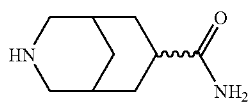 | 3-azabicyclo[3.3.1]nonane-7-carboxamide | 40.5 | 76.9 | >10,000 | 169 | |
| 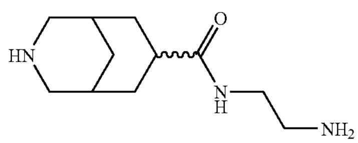 | N-(2-aminoethyl)-3-azabicyclo[3.3.1]nonane-7-carboxamide | ND | 52.4 | ND; failed HTS | 212 | 3.52-3.40 (m, 2H), 3.30-3.05 (m, 6H), 2.85-2.74 (m, 1H), 2.34-2.02 (m, 4H), 1.88-1.64 (m, 4H) |
| 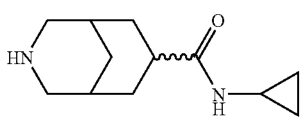 | N-cyclopropyl-3-azabicyclo[3.3.1]nonane-7-carboxamide | 706.9 | 15.6 | ND; failed HTS | 209 | |
| 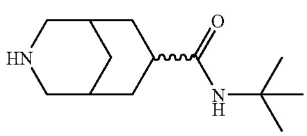 | N-tert-butyl-3-azabicyclo[3.3.1]nonane-7-carboxamide | 10.9 | 7.1 | ND; failed HTS | 225 | 3.45-3.10 (m, 4H), 3.78 (m, 1H), 2.42-2.12 (m, 4H), 1.85-1.64 (m, 4H), 1.32 (s, 9H) |
| 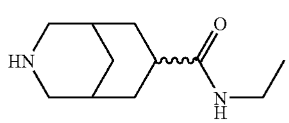 | N-ethyl-3-azabicyclo[3.3.1]nonane-7-carboxamide | 13.5 | 6.4 | ND; failed HTS | 197 | |
| 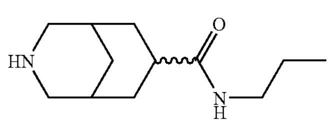 | N-propyl-3-azabicyclo[3.3.1]nonane-7-carboxamide | 21.4 | 10.4 | ND; failed HTS | 211 | 3.25-3.10 (m, 4H), 2.85-2.75 (m, 1H), 2.40-2.18 (m, 4H), 1.85-1.42 (m, 8H), 0.95 (t, 3H) |
| 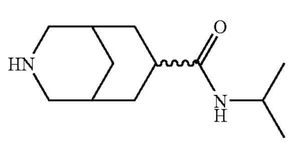 | N-isopropyl-3-azabicyclo[3.3.1]nonane-7-carboxamide | 82 | 31 | ND; failed HTS | 211 | 4.0-3.9 (m, 1H), 3.35-3.20 (m, 4H), 2.80-2.70 (m, 1H), 2.32-2.14 (m, 4H), 1.85-1.66 (m, 4H), 1.15 (d, 6H) |
| 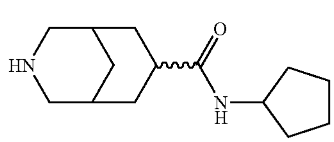 | N-cyclopentyl-3-azabicyclo[3.3.1]nonane-7-carboxamide | 102.3 | 26.8 | ND; failed HTS | 237 | |
| 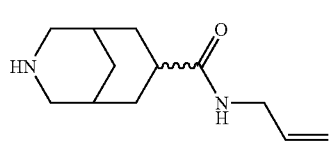 | N-allyl-3-azabicyclo[3.3.1]nonane-7-carboxamide | 30.6 | 4.3 | ND; failed HTS | 209 | |

TABLE 6-continued

| Structure | Name | Rat α4β2 Ki | Human α4β2 Ki | α7 Ki | MS: m/z (M + H) | ¹H NMR: CD₃OD, 300 MHz, δ |
|---|---|---|---|---|---|---|
| 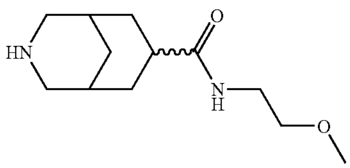 | N-(2-methoxyethyl)-3-azabicyclo[3.3.1]nonane-7-carboxamide | 457.1 | 773.7 | ND; failed HTS | 227 | |
| 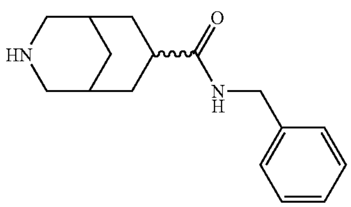 | N-benzyl-3-azabicyclo[3.3.1]nonane-7-carboxamide | 884.6 | 9 | ND; failed HTS | 259 | |
| 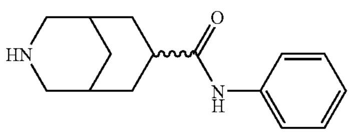 | N-phenyl-3-azabicyclo[3.3.1]nonane-7-carboxamide | ND | 12.7 | ND; failed HTS | 245 | |
| 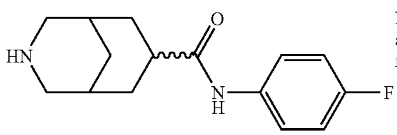 | N-(4-fluorophenyl)-3-azabicyclo[3.3.1]nonane-7-carboxamide | 92.2 | 32.1 | ND; failed HTS | 263 | |
| 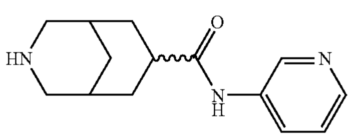 | N-(pyridin-3-yl)-3-azabicyclo[3.3.1]nonane-7-carboxamide | ND | 46.8 | ND; failed HTS | 246 | |
| 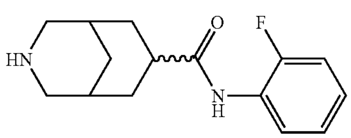 | N-(2-fluorophenyl)-3-azabicyclo[3.3.1]nonane-7-carboxamide | 63 | 24.1 | ND; failed HTS | 263 | 7.78 (m, 1H), 7.24-7.10 (m, 3H), 3.38-3.05 (m, 5H), 2.45-2.20 (m, 4H), 1.98-1.82 (m, 4H) |
| 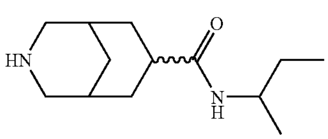 | N-sec-butyl-3-azabicyclo[3.3.1]nonane-7-carboxamide | 271.6 | 42.8 | >10,000 | 225 | 3.80 (m, 1H), 3.15-3.05 (m, 4H), 2.80 (m, 1H), 2.338-2.15 (m, 4H), 1.98-1.65 (m, 4H), 1.58-1.42 (m, 2H), 1.15 (d, 3H), 0.9 (t, 3H) |
| 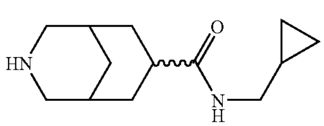 | N-(cyclopropylmethyl)-3-azabicyclo[3.3.1]nonane-7-carboxamide | 69.1 | 92.2 | ND; failed HTS | 223 | |
| 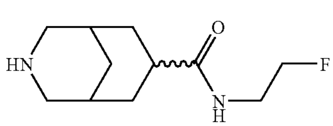 | N-(2-fluoroethyl)-3-azabicyclo[3.3.1]nonane-7-carboxamide | 121.7 | 13.5 | >10,000 | 215 | |
| 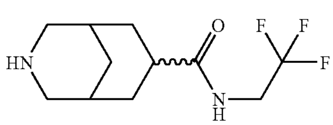 | N-(2,2,2-trifluoroethyl)-3-azabicyclo[3.3.1]nonane-7-carboxamide | 40.8 | 22.8 | >10,000 | 251 | |

TABLE 6-continued

| Structure | Name | Rat α4β2 Ki | Human α4β2 Ki | α7 Ki | MS: m/z (M + H) | ¹H NMR: CD$_3$OD, 300 MHz, δ |
|---|---|---|---|---|---|---|
| 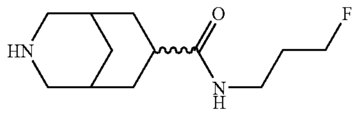 | N-(3-fluoropropyl)-3-azabicyclo[3.3.1]nonane-7-carboxamide | 44.7 | 23.2 | ND; failed HTS | 229 | |
| 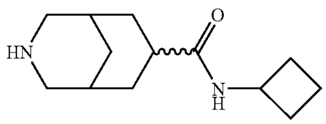 | N-(cyclobutyl)-3-azabicyclo[3.3.1]nonane-7-carboxamide | 134.6 | 307.7 | ND; failed HTS | 223 | 4.35-4.22 (m, 1H), 3.25-3.08 (m, 4H), 2.80-2.70 (m, 1H), 2.42-2.15 (m, 6H), 2.05-1.65 (m, 8H) |
| 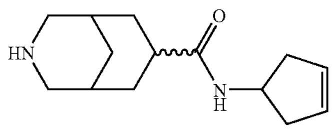 | N-(3-cyclopentenyl)-3-azabicyclo[3.3.1]nonane-7-carboxamide | 45.3 | 24.3 | ND; failed HTS | 235 | |
| 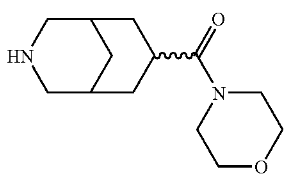 | 4-morpholinyl(3-azabicyclo[3.3.1]non-7-yl)methanone | 62.5 | 22.5 | ND; failed HTS | 239 | |

Example 13

Ketone derivatives of 3-azabicyclo[3.3.1]nonan-7-carboxylic acid

Certain acyl (ketone) derivatives of 3-azabicyclo[3.3.1]nonane-7-carboxylic acid can be prepared by reaction of N-methoxy-N-methyl-3-(tert-butoxycarbonyl)-3-azabicyclo[3.3.1]nonane-7-carboxamide with aryl- and alkyllithium reagents. The following procedure is exemplary.

2-Furanyl(3-azabicyclo[3.3.1]non-7-yl)methanone trifluoroacetate

To a suspension of N,O-dimethylhydroxylamine hydrochloride (0.068 g 0.70 mmol) in anhydrous THF (3 mL) was added trimethylaluminum (2.0 M solution in toluene, 0.35 mL, 0.70 mmol) at −10° C. After stirring for 10 min at −10° C., a solution of methyl (3-(tert-butoxycarbonyl)-3-azabicyclo[3.3.1]nonane-7-carboxylate (0.100 g, 0.353 mmol) in THF (1 mL) was added. The reaction mixture was warmed to ambient temperature and stirred for 1 h. The reaction was then cooled to −70° C. and was treated with a freshly prepared 2-furanyllithium in THF (5 mL) solution (Note: the 2-furanyllithium was prepared by treating furan (0.24 g, 3.5 mmol) with n-BuLi (2.5 M solution in THF, 1.4 mL, 3.5 mmol) at −78° C.). The reaction mixture was warmed to ambient temperature over 1 h and quenched with saturated aqueous ammonium chloride solution (5 mL). The volatiles were removed in vacuo, and the residue was triturated with ethyl acetate (2×10 mL). The combined organic extracts were dried over anhydrous sodium sulfate, concentrated under reduced pressure and purified by HPLC, to yield 2-furanyl(3-(tert-butoxycarbonyl)-3-azabicyclo[3.3.1]non-7-yl)methanone (0.018 g, 16% yield). A portion of this material (4.5 mg, 14 µmol) was dissolved in a 1:1 mixture of anhydrous dichloromethane and TFA. After stirring for 1 h at ambient temperature, the volatiles were evaporated, and the resulting residue was dried on high vacuum to yield 3.2 mg (68% yield) of 2-furanyl(3-azabicyclo[3.3.1]non-7-yl)methanone trifluoroacetate as a pale yellow oil (¹H NMR (CD$_3$OD): δ 7.68 (s, 1H), 6.75 (d, J=2.68 Hz, 1H), 6.58 (m, 1H), 4.16-4.11 (m, 1H), 3.52-3.14 (m 3H), 2.64-2.57 (m 1H), 2.25-1.87 (m, 8H) (LC/MS (MH⁺): 220).

Procedures similar to the above were used to make a variety of acyl (ketone) derivatives, including the compounds in Table 7.

TABLE 7

| Structure | Name | Rat α4β2 Ki | Human α4β2 Ki | α7 Ki | MS: m/z (M + H) |
|---|---|---|---|---|---|
| 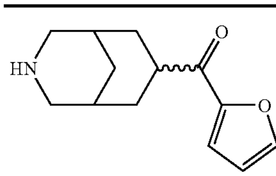 | 2-furanyl(3-azabicyclo[3.3.1]non-7-yl)methanone | ND | 113.4 | >10,000 | 220 |

TABLE 7-continued

| Structure | Name | Rat α4β2 Ki | Human α4β2 Ki | α7 Ki | MS: m/z (M + H) |
|---|---|---|---|---|---|
| 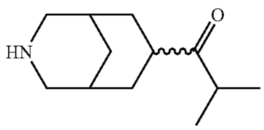 | 1-(3-azabicyclo[3.3.1]non-7-yl)-2-methyl-1-propanone | ND | 78.9 | >10,000 | 196 |

Example 14

Summary of Receptor Binding

Compounds of Tables 1-7, representative of the present invention, exhibit inhibition constants (Ki values) at the α4β2 subtype (rat or human or both) in the range of 1 nM to 2000 nM. The great majority of these compounds exhibit Ki values at the α4β2 subtype (rat or human or both) of less than 500 nM, and many exhibit Ki values of less than 100 nM. The compounds in Tables 1-7 often fail to pass high throughput screening (HTS) criteria for generating Ki values at the α7 subtype. In those cases where HIS criteria at the α7 subtype were met, the Ki values subsequently determined at the α7 subtype were greater than 10 μM (>10,000 nM). In general, these same compounds exhibit relatively little functional activity at either human muscle or human ganglion subtypes, the exception being compounds in Table 5. However, even the unsaturated analogs were, in general, more potent at the α4β2 subtype than at muscle or ganglion subtypes.

The notation "failed HTS" as used herein for α7 subtype binding means that the compound failed to inhibit, at 5 μM concentration, the binding of 5 nM $^3$H-MLA (methyllycaconitine) by at least 50%.

Certain exemplified compounds were assessed in the NOR (novel object recognition) task. This illustrates efficacy and potency of the compounds of the present invention in treating cognitive deficits, attention disorders, and dementias, and the potential of these compounds for human therapy.

FIG. 1 shows that Compound A, methyl 3-azabicyclo[3.3.0]octane-7-carboxylate, is active in the NOR task (orally, in rats) at a dose of 0.1 mg/kg. The results are shown as a function of recognition index (%) versus dose (mg/kg).

Figure 2:
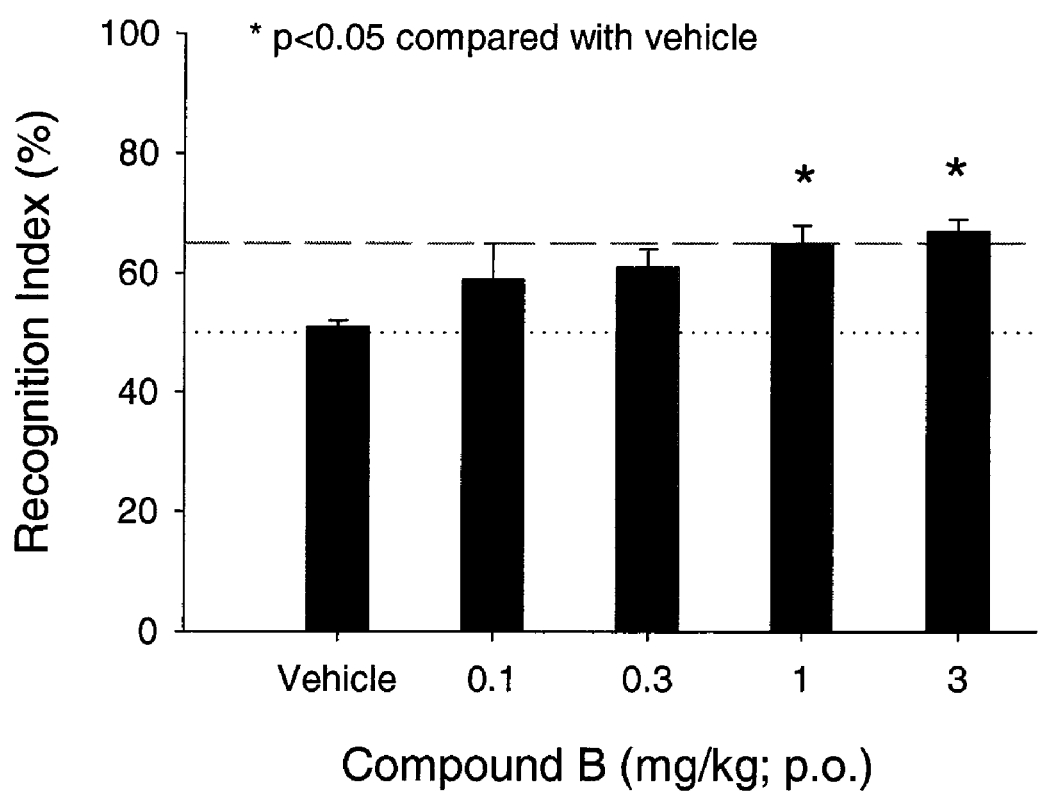
FIG. 2 is a chart showing the results of a study on novel object recognition in rats treated orally with Compound B, N-methyl-3-azabicyclo[3.3.1]nonane-7-carboxamide. The results are shown as a function of recognition index (%) versus dose (mg/kg).

FIG. 2 shows that Compound B, N-methyl-3-azabicyclo[3.3.1]nonane-7-carboxamide, is active in the NOR task (orally, in rats) at a dose of 1 mg/kg. The results are shown as a function of recognition index (%) versus dose (mg/kg).

Test compounds were employed in free or salt form.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

The invention claimed is:

1. A compound, N-propyl-3-azabicyclo[3.3.1]nonane-7-carboxamide or a pharmaceutically acceptable salt thereof.

2. A pharmaceutical composition comprising N-propyl-3-azabicyclo[3.3.1]nonane-7-carboxamide or a pharmaceutically acceptable salt thereof, and one or more pharmaceutically acceptable diluent, excipient, or inert carrier.

3. A method for treating a central nervous system disorder, comprising administering N-propyl-3-azabicyclo[3.3.1]nonane-7-carboxamide or a pharmaceutically acceptable salt thereof, wherein the disorder is selected from the group consisting of age-associated memory impairment, mild cognitive impairment, pre-senile dementia, early onset Alzheimer's disease, senile dementia, dementia of the Alzheimer's type, Lewy body dementia, vascular dementia, Alzheimer's disease, stroke, and AIDS dementia complex.

4. A method for treating a disorder, comprising administering N-propyl-3-azabicyclo[3.3.1]nonane-7-carboxamide or a pharmaceutically acceptable salt thereof, wherein the disorder is selected from the group consisting of attention deficit disorder, attention deficit hyperactivity disorder, and dyslexia.

5. A method for treating a disorder, comprising administering N-propyl-3-azabicyclo[3.3.1]nonane-7-carboxamide or a pharmaceutically acceptable salt thereof, wherein the disorder is selected from the group consisting of schizophrenia, cognitive deficits in schizophrenia, cognitive dysfunction in schizophrenia, schizophreniform disorder, and schizoaffective disorder.

* * * * *